United States Patent
Burns et al.

(10) Patent No.: US 11,896,974 B2
(45) Date of Patent: Feb. 13, 2024

(54) MICROFLUIDIC DEVICE FOR SIZE AND DEFORMABILITY MEASUREMENTS AND APPLICATIONS THEREOF

(71) Applicant: REGENTS OF THE UNIVERSITY OF MICHIGAN, Ann Arbor, MI (US)

(72) Inventors: Mark A. Burns, Ann Arbor, MI (US); Alyse D. Krausz, Ann Arbor, MI (US); Sarah Elizabeth Mena, Ann Arbor, MI (US); Martin Patrick De Beer, Ann Arbor, MI (US); Kevin R. Ward, Superior Township, MI (US); Frederick Korley, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 17/859,400

(22) Filed: Jul. 7, 2022

(65) Prior Publication Data
US 2022/0347688 A1 Nov. 3, 2022

Related U.S. Application Data

(62) Division of application No. 16/746,408, filed on Jan. 17, 2020, now Pat. No. 11,389,799.
(Continued)

(51) Int. Cl.
*B01L 3/00* (2006.01)
*G01N 33/543* (2006.01)
(Continued)

(52) U.S. Cl.
CPC ... *B01L 3/502761* (2013.01); *B01L 3/502707* (2013.01); *B01L 3/502715* (2013.01);
(Continued)

(58) Field of Classification Search
CPC ......... B01L 3/502761; B01L 3/502707; B01L 3/502715; B01L 2200/0668;
(Continued)

(56) References Cited

U.S. PATENT DOCUMENTS 7,188,515 B2  3/2007  Burns et al.
8,056,398 B2  11/2011  Jakli et al.
(Continued)

FOREIGN PATENT DOCUMENTS

CN  102695804 A  * 9/2012  ........ B01L 3/502715
CN  104083809 A  * 10/2014  ....... A61B 5/150755
(Continued)

OTHER PUBLICATIONS

Translation of CN102695804A, Hvichia, G, Sep. 26, 2012 (Year: 2012).*
(Continued)

*Primary Examiner* — Samuel P Siefke
*Assistant Examiner* — Henry H Nguyen
(74) *Attorney, Agent, or Firm* — MARSHALL, GERSTEIN & BORUN LLP

(57) ABSTRACT

A microfluidic device system includes a channel having an entrance and an exit, a height at the entrance being greater than a height at the exit. The height of the channel may decrease continuously from the height at the entrance to the height at the exit. Cells or particles or beads traveling through the channel become trapped based on their size and/or deformability. A visual sensor captures images of the trapped cells or particles or beads, and image software analyzes the captured images to provide size and/or deformability and/or fluorescence information. A method of fabricating such a microfluidic device includes introducing a
(Continued)

glass wafer to an etching solution at a specific rate such that a first end of the glass wafer is etched longer than other portions of the glass wafer.

19 Claims, 14 Drawing Sheets

Related U.S. Application Data

(60) Provisional application No. 62/908,406, filed on Sep. 30, 2019, provisional application No. 62/793,720, filed on Jan. 17, 2019.

(51) Int. Cl.
  *G01N 33/68* (2006.01)
  *G01N 21/64* (2006.01)
  *G01N 1/28* (2006.01)
  *G01N 15/14* (2006.01)

(52) U.S. Cl.
  CPC ............ *G01N 1/28* (2013.01); *G01N 15/1475* (2013.01); *G01N 21/6428* (2013.01); *G01N 33/54366* (2013.01); *G01N 33/6803* (2013.01); *B01L 2200/0668* (2013.01); *B01L 2200/12* (2013.01); *B01L 2300/0627* (2013.01); *G01N 2015/1493* (2013.01); *G01N 2021/6439* (2013.01)

(58) Field of Classification Search
  CPC ......... B01L 2200/12; B01L 2300/0627; G01N 1/28; G01N 15/1475; G01N 21/6428; G01N 33/54366; G01N 33/6803; G01N 2015/1493; G01N 2021/6439; G01N 33/54393; G01N 2015/1006; G01N 2015/1495
  See application file for complete search history.

(56) References Cited

U.S. PATENT DOCUMENTS

| | | | |
|---|---|---|---|
| 8,454,906 | B2 | 6/2013 | Mathies et al. |
| 8,961,903 | B2 | 2/2015 | Sadaba Champetier De Ribes et al. |
| 2008/0014589 | A1 | 1/2008 | Link et al. |
| 2008/0311006 | A1 | 12/2008 | Bek et al. |
| 2009/0092989 | A1 | 4/2009 | Chang et al. |
| 2011/0201009 | A1 | 8/2011 | Quake et al. |
| 2012/0052567 | A1* | 3/2012 | Hvichia ............... C12N 5/0603 435/325 |
| 2012/0322682 | A1 | 12/2012 | McDevitt et al. |
| 2014/0018299 | A1 | 1/2014 | Mondello et al. |
| 2015/0044696 | A1 | 2/2015 | Dothie et al. |
| 2015/0196913 | A1 | 7/2015 | Liu et al. |
| 2016/0069873 | A1* | 3/2016 | Takada ............... B01L 3/502761 435/7.1 |
| 2018/0106818 | A1 | 4/2018 | Datwyler et al. |
| 2018/0372758 | A1* | 12/2018 | Larsen ............... B01L 3/502707 |

FOREIGN PATENT DOCUMENTS

| | | |
|---|---|---|
| WO | WO-2011/091037 A2 | 7/2011 |
| WO | WO-2014/194329 | 12/2014 |
| WO | WO-2018/195530 A1 | 10/2018 |

OTHER PUBLICATIONS

Bell et al., Interleukin-6 and interleukin-10 in cerebrospinal fluid after severe traumatic brain injury in children, J. Neurotrauma, 14(7):451-7 (Jul. 1997).

Bland et al., Statistical methods for assessing agreement between two methods of clinical measurement, Lancet, 1(8476):37-10 (Feb. 1986).

Bogoslovsky et al., Fluid Biomarkers of Traumatic Brain Injury and Intended Context of Use. Diagnostic, 6:37 (2016).

Brophy et al., Biokinetic analysis of ubiquitin C-terminal hydrolase-L1 (UCH-L1) in severe traumatic brain injury patient biofluids, J. Neurotrauma, 28(6):861-70 (Jun. 2011).

Böhmer et al., Neuron-specific enolase, S100B, and glial fibrillary acidic protein levels as outcome predictors in patients with severe traumatic brain injury, Neurosurgery, 68(6):1624-30 (Jun. 2011).

Giacoppo et al., Predictive biomarkers of recovery in traumatic brain injury, Neurocrit Care, 16(3):470-7 (Jun. 2012).

Khetani et al., Polyethylenimine Modified Graphene-Oxide Electrochemical Immunosensor for the Detection of Glial Fibrillary Acidic Protein in Central Nervous System Injury, ACS Sens., 3(4):844-51 (2018).

Kim et al., Magnetic bead-quantum dot assay for detection of a biomarker for traumatic brain injury, Nanoscale, 7(42):17820-6 (Nov. 2015).

Korfias et al., Slight and short-lasting increase of serum S-100B protein in extra-cranial trauma, Brain Inj., 20(8):867-72 (Jul. 2006).

Korley et al., Performance Evaluation of a Multiplex Assay for Simultaneous Detection of Four Clinically Relevant Traumatic Brain Injury Biomarkers, J. Neurotrauma, 36:182-7 (Jul. 2018).

Lei et al., Glial fibrillary acidic protein as a biomarker in severe traumatic brain injury patients: a prospective cohort study, Crit. Care, 19:362 (Oct. 2015).

Ma et al., Carbon dots based immunosorbent assay for the determination of GFAP in human serum, Nanotechnology, 29(14):145501 (Apr. 2018).

McKee et al., Emerging Roles for the Immune System in Traumatic Brain Injury, Front Immunol., 7:556 (Dec. 2016).

Microfluidics Market Size, Share & Trends Analysis Report by Material (Polymer, Glass, Silicon, Metal, Ceramic), By Application (Pharmaceutical, In-Vitro diagnostics), By Region, And Segment Forecasts, 2019-2026, Grandview Research, 122 pages (Jun. 2019).

Missler et al., Measurement of glial fibrillary acidic protein in human blood: analytical method and preliminary clinical results, Clin. Chem., 45(1):138-41 (Jan. 1999).

Mondello et al., Blood-based diagnostics of traumatic brain injuries, Expert. Rev. Mol. Diagn., 11(1):65-78 (Jan. 2011).

Obahiagbon et al., A compact, low-cost, quantitative and multiplexed fluorescence detection platform for point-of-care applications, Biosens. Bioelectron., 117:153-60 (2018).

Obahiagbon et al., Considerations for Low-cost Reader Design and Label Selection for Lateral Flow Assays, 2018 IEEE Biomedical Circuits and Systems Conference, BioCAS 2018—Proceedings, pp. 1-4 (2018).

Pal et al., Phase Change Microvalve for Integrated Devices, Anal. Chem., 76(13):3740-8 (2004).

Papa et al., Time Course and Diagnostic Accuracy of Glial and Neuronal Blood Biomarkers GFAP and UCH-L1 in a Large Cohort of Trauma Patients With and Without Mild Traumatic Brain Injury, JAMA Neurol., 73(5):551-60 (May 2016).

Passing et al., A new biometrical procedure for testing the equality of measurements from two different analytical methods. Application of linear regression procedures for method comparison studies in clinical chemistry, Part I, J. Clin. Chem. Clin. Biochem., 21(11):709-20 (Nov. 1983).

Rissin et al., Single-molecule enzyme-linked immunosorbent assay detects serum proteins at subfemtomolar concentrations, Nat. Biotechnol., 28(6):595-9 (Jun. 2010).

Roth et al., Improving the Sensitivity of Fluorescence-Based Immunoassays by Photobleaching the Autofluorescence of Magnetic Beads, Small, 15:1803751 (2019).

Russomanno et al., The design of pressure-controlled valves for a refreshable tactile display, 2015 IEEE World Haptics Conference IEEE, pp. 177-182 (2015).

Sharma et al., Biomarkers in traumatic brain injury, Curr. Neurol. Neurosci. Rep., 12(5):560-9 (Oct. 2012).

Srivastava et al., Analysis of Non-Newtonian Liquids Using a Microfluidic Capillary Viscometer, Anal. Chem., 78(5):1690-6 (Mar. 2006).

(56) References Cited

OTHER PUBLICATIONS

Srivastava et al., Nanoliter viscometer for analyzing blood plasma and other liquid samples, Anal. Chem., 77(2):383-92 (Jan. 2005).

Su et al., Cost-Effectiveness of Biomarker Screening for Traumatic Brain Injury, J. Neurotrauma, 36(13):2083-91 (Jul. 2019).

Venkatasubbarao et al., Field-based multiplex and quantitative assay platforms for diagnostics, p. 80290P, In: Southern et al. (eds.), Sens Technol Glob Heal Mil Med Disaster Response, Environ Monit Biometric Technol Hum Identif VIII. International Society for Optics and Photonics (2011).

Welch et al., Orientation and characterization of immobilized antibodies for improved immunoassays (Review), Biointerphases, 12:02D301 (2017).

Wilson et al., The Simoa HD-1 Analyzer: A Novel Fully Automated Digital Immunoassay Analyzer with Single-Molecule Sensitivity and Multiplexing, J. Lab. Autom., 21(4):533-47 (Aug. 2016).

Zetterberg et al., Fluid biomarkers for mild traumatic brain injury and related conditions, Nat. Rev. Neurol., 12(10):563-74 (Oct. 2016).

Krausz et al., A point-of-care microfluidic system for traumatic brain injury diagnosis and prognosis, University of Michigan MBSTP Symposium 2019 (May 2019).

Krausz et al., A point-of-care microfluidic device for high frequency measurement of biofluid biomarkers, 2019 Massey TBI Grand Challenge Kickoff (Feb. 22, 2019).

Srivastava et al., Electronic drop sensing in microfluidic devices: automated operation of a nanoliter viscometer, Lab Chip, 6(6):744-51 (Jun. 2006).

Livak-Dahl et al., Nanoliter droplet viscometer with additive-free operation, Lab Chip, 13:297-301 (2013).

Pinto et al., "The application of microbeads to microfluidic systems for enhanced detection and purification of biomolecules", Dec. 2016, Methods, 116, (2017) pp. 112-124.

Liu et al., "Magnetic bead-based DNA detection with multi-layers quantum dots labeling for rapid detection of *Escherichia coli* o157: H7", Jun. 2008, Biosensors and Bioelectronics, 24, pp. 558-565 (2008).

\* cited by examiner

MICROFLUIDIC DEVICE FOR SIZE AND DEFORMABILITY MEASUREMENTS AND APPLICATIONS THEREOF

CROSS-REFERENCE TO RELATED APPLICATIONS

This application is a division of U.S. patent application Ser. No. 16/746,408 filed Jan. 17, 2020, which claims the benefit of the filing dates of U.S. Provisional Application No. 62/793,720, filed Jan. 17, 2019, and U.S. Provisional Application No. 62/908,406, filed Sep. 30, 2019, the disclosures of which are hereby incorporated by reference in their entireties.

STATEMENT OF GOVERNMENT INTEREST

This invention was made with government support under DK046960 awarded by the National Institutes of Health. The government has certain rights in the invention.

FIELD OF THE DISCLOSURE

This application relates to a microfluidic device for determining the presence, size and/or deformability of cells or particles within a solution. A method of use and a method of fabricating a microfluidic device for purposes of determining the presence, size and/or deformability of cells, proteins, or particles within a solution is also provided.

BACKGROUND

Traumatic brain injury (TBI) causes significant morbidity and mortality globally. In the United States alone, an estimated 1.9 million people sustain a TBI annually, and 50,000 of these individuals die of their injuries. Furthermore, 2% of the United States population is estimated to have a disability caused by TBI. The high rates of morbidity and mortality can be attributed to ineffective diagnostic and treatment methods. No new treatments for TBI have been approved in 30 years, largely due to the heterogeneity of injuries and insensitive nature of TBI diagnosis and classification. Assessment of TBI injuries is typically done through neurological examination and neuroimaging techniques. While these methods are capable of identifying direct tissue damage to the brain, they cannot assess the secondary damage stemming from the initial injury. The primary tissue damage sets off a cascade of secondary injuries, such as neuronal cell death, blood brain barrier breakdown, edema, and upregulation of inflammatory markers. Protein biomarkers have been proposed as a way of monitoring the progression of secondary TBI injury and of providing more sensitive diagnostic measures when used in conjunction with imaging and physical examination. FDA approved biomarkers, glial fibrillary acidic protein (GFAP) and ubiquitin c-terminal hydrolase L1 (UCH-L1), can currently only be measured in a hospital laboratory. However, GFAP is detectable in serum within one hour after injury, enabling the possibility of point-of-care diagnosis in pre-hospital and field settings.

SUMMARY

The current disclosure is directed to a microfluidic device for determining the size, and/or deformability, of cells or particles. The microfluidic device includes a channel having an entrance and an exit, a height at the entrance being greater than a height at the exit. The height of the channel may decrease continuously from the height at the entrance to the height at the exit. Cells or particles traveling through the channel become trapped based on their size and/or deformability. A visual sensor captures images of the trapped cells or particles, and image software analyzes the captured images to provide size and/or deformability information. A method of fabricating such a microfluidic device includes introducing a glass wafer to an etching solution at a specific rate such that a first end of the glass wafer is etched longer than other portions of the glass wafer.

The microfluidic device could be used in a variety of applications. For example, the microfluidic device could be used to determine the poly-dispersity of microbeads. Commercial manufacturers of microbeads that prefer a narrow distribution of particle size in their fabrication could use the microfluidic device to check the quality of their microbeads. As another example, the microfluidic device could be used to separate whole blood into white blood cells and red blood cells since white blood cells have a size of approximately 10 μm while red blood cells have a size of approximately 2 μm. As yet another example, circulating tumor cells could be separated from other cells using the microfluidic device. Further studies on the deformability of the tumor cells could also be carried out by the device.

Another potential use of the microfluidic device would be to carry out spectrophotometric measurements. Based on the Beers-Lambert law, the light absorbed by a liquid is a function of the concentration, the path length, and the absorptivity of the liquid. Following this principle, at different positions in the channel of the microfluidic device, the absorbed light is a function of the thickness of the liquid (the height of the channel). Applications of the spectrophotometric measurements could include the measurement of the concentration of different solutions (including blood, i.e. hematocrit content), and any other solution.

Further still, the device can be used in assays, such as immunoassays, to detect and diagnose various conditions, such as traumatic brain injury. Accordingly, the disclosure is further directed to a microfluidic assay. The microfluidic assay can comprise a solution comprising a target protein, a first complex, and a second complex. The first complex comprises a bead, wherein the bead has a diameter and a surface. The surface of the bead can be substantially coated in a first molecule, such as an antibody, DNA (or fragment thereof), or RNA (or fragment thereof). The second complex can comprise a second molecule, such as an antibody, DNA (or fragment thereof), or RNA (or fragment thereof), associated with a quantum dot. When exposed to the target protein (i.e., within the solution), the first molecule and the second molecule can associate with the target protein to form a multiplex on the surface of the bead.

The disclosure also provides methods of using a microfluidic assay within the microfluidic device. The method comprises providing a microfluidic device system having a channel. The channel has a height that is greater at an entrance to the channel than a height at an exit of the channel. The channel can decrease in height from the entrance to the exit. The method also comprises combining a first solution with a target protein and a second solution. The first solution comprises a plurality of beads, wherein each bead has a diameter and a surface substantially coated with a first molecule. The second solution comprises a second molecule associated with a quantum dot. Upon combining the first solution with the target protein and the second solution, the first molecule (e.g. in the first solution) and the second molecule (e.g. in the second solution) associate with the target protein to form a multiplex on the surface of each of the plurality of beads. The method comprises trapping each bead of the plurality of beads along the channel based on the diameter of the bead. The method comprises capturing an image of the trapped plurality of beads, sending the image to a data collection/readout device, and analyzing the image using image software to measure the fluorescence of the multiplex on the surface of at least one of the trapped beads located at one or more locations along the channel.

Also provided is a kit for determining the concentration of a target protein in a solution comprising the microfluidic assay and microfluidic device described herein.

Further aspects and advantages will be apparent to those of ordinary skill in the art from a review of the following detailed description. The description hereafter includes specific embodiments with the understanding that the disclosure is illustrative, and is not intended to limit the invention to the specific embodiments described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE PREFERRED EMBODIMENTS

Microfluidic Device System

Figure 1:
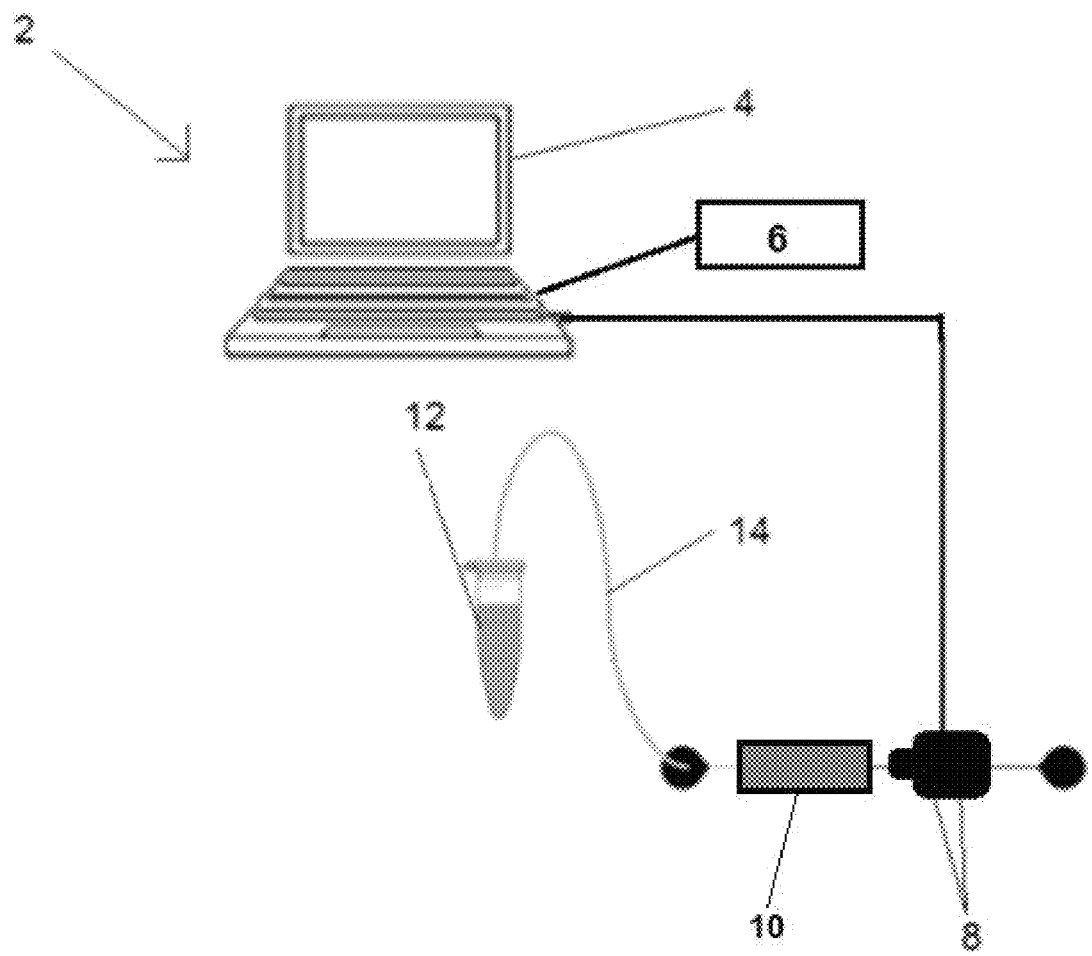
FIG. 1 illustrates schematically a microfluidic device system including a microfluidic device, a data collection and readout device having image software, a visual sensor, and multiple inlets and supply lines through which solutions can be provided to the microfluidic device.

Referring to the figures in detail, FIG. 1 illustrates an exemplary microfluidic device system 2 including a data collection/readout device 4, such as a computer or a portable electronic device, connected to a visual sensor 8. The visual sensor 8 can be, for example, an inverted light microscope or a camera, and the data collection/readout device 4 includes image analysis software and/or image capture software 6 (collectively image software 6) such as IMAGEJ and OCAPTURE. The visual sensor 8 collects images of particles, cells, or beads in microfluidic device 10. The particles, cells, or beads are introduced from a container 12 via a supply line 14. The visual sensor 8 collects images of the locations along the microfluidic device 10 at which the particles, cells, or beads stop movement. The images are sent to the data collection/readout device 4, and the size and/or deformability of the particles, cells, or beads is calculated by the image software 6. In some instances, different subpopulations of cells, particles, or beads may be identified based on deformability, size, and/or fluorescence. Information about the particles, cells, or beads may be displayed or transmitted to the Internet or cloud storage by the data collection/readout device 4.

The microfluidic device 10 may be fabricated from glass wafers. The glass device 10 may include a first glass wafer that is fabricated to have patterned channels according to the fabrication method disclosed below and a second glass wafer that has inlet and outlet holes drilled into it. An inlet port for the supply line 14 may be created by gluing shoulder washers on top of the inlet hole in the second glass wafer or by using a CorSolutions microfluidic connector system. Pressures at the inlet port may be measured using a digital pressure gauge.

Figure 2:
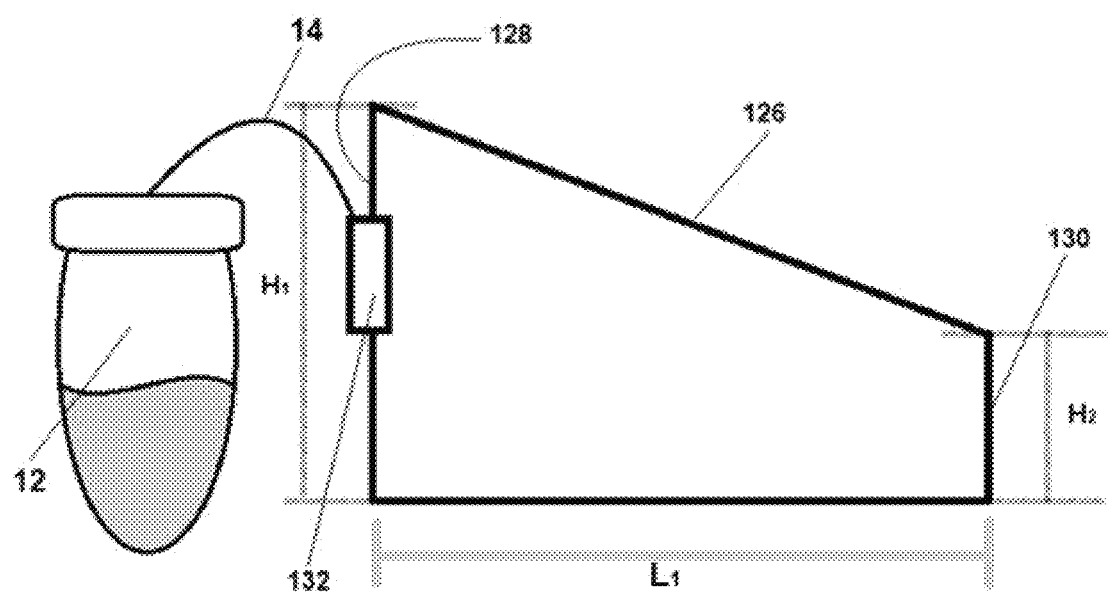
FIG. 2 illustrates a channel in the microfluidic device having a continuous decrease in height from an entrance to the channel to the exit of the channel.
Figure 3A:
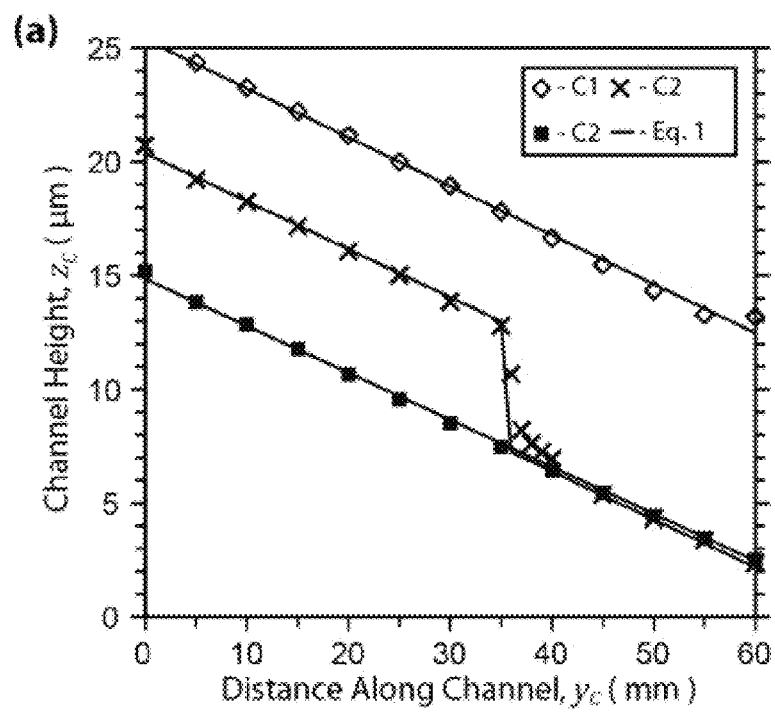
FIG. 3A is a graph showing linear height profiles of channels of microfluidic devices.
Figure 3B:
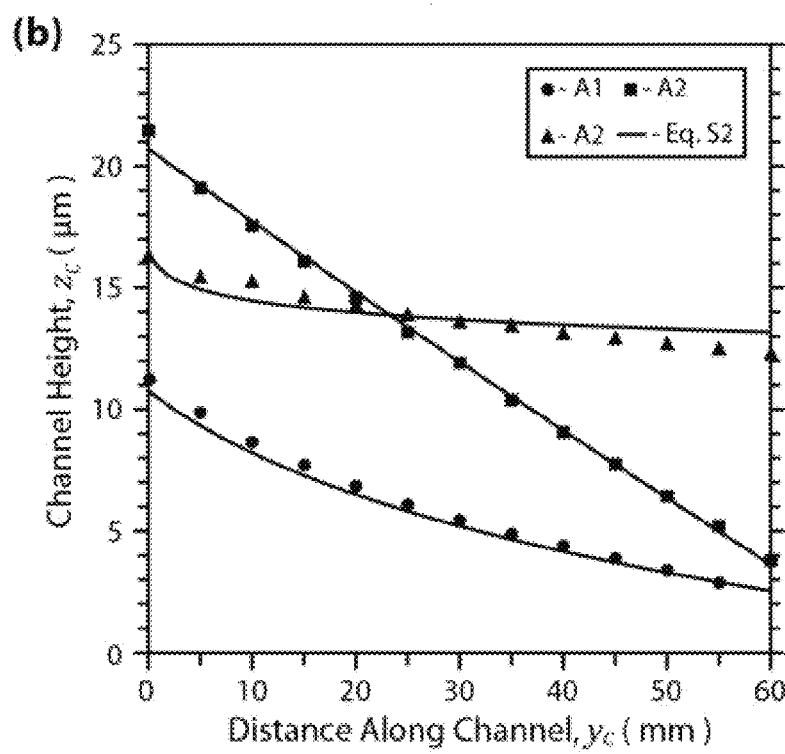
FIG. 3B is a graph showing quadratic height profiles of channels of microfluidic devices.

As shown in FIG. 2, the microfluidic device 10 includes a channel 126 that has a higher height $H_1$ at the entrance 128 to the channel 126 than the lower height $H_2$ at the exit 130 to the channel 126. Generally, the change in height is smooth and continuous from the entrance 128 to the exit 130 as shown in FIG. 2. FIG. 3A shows two height profiles, C1 and C2, for a microfluidic device 10 that are continuously linear. In some rare instances, the change in height may be stepwise with incremental decreases in the height of the channel 126. FIG. 3A shows one height profile, C2, for a microfluidic device 10 that includes an incremental decrease. As yet another example, FIG. 3B shows two height profiles, A1 and A2, having a quadratic profile. The slope of the channel 126 may be specifically tailored to the solution or assay being analyzed by the microfluidic device system 2. For example, the slope may be steeper for solutions or assays in which cells and/or particles and/or beads have greatly different sizes and/or deformability, whereas the slope may be gentler for solutions having minor differences in the size or deformability of the cells or particles. Particles and/or cells and/or beads are introduced to the channel 126 through inlet 132. As particles or cells or beads flow through the channel 126, the particles or cells or beads become trapped at a height corresponding to their size or level of deformability.

The channel 126 is at least 1000 μm wide in order to allow many particles and cells and beads to be tested without clogging the channel 126. The channel 126 should be wide enough to allow smaller particles, cells, and/or beads to flow past larger trapped particles, cells, and/or beads. The width of the channel and the number of larger particles, cells, and/or beads should be such that even when all of the larger particles, cells, and/or beads are trapped, the channel 126 is not fully blocked. In some instances, the width of the channel 126 may vary. For example, the channel 126 may be wider in areas where many particles, cells, and/or beads are anticipated to become trapped. The width of the channel 126 may be adjusted to ensure that the particles, cells, and/or beads will become trapped in a straight line across the channel 126, thereby making the results of using the microfluidic device 10 easier to analyze. The depth of the channel 126 is much less than the width. In some instances, the depth of the downstream channel is 1 μm. The analysis of the size and/or deformability of the particles or cells or beads occurs by visually observing the distance that the cells or particles traveled before getting stopped. Measurements of variations in sizes and/or deformability within one population of particles or cells are also possible thanks to the continuous slope of the channel that can be varied to achieve different resolutions.

When used with a microfluidic immunoassay, discussed below, the height $H_1$ of the channel 126 at the entrance 128 may depend on the particular bead and diameter thereof that is being used in the immunoassay. In some instances, the height $H_1$ at the entrance 128 may be between 4 μm and 15 μm. Likewise, the height $H_2$ at the exit 130 may depend on the particular bead and diameter thereof that is being used in the immunoassay. The height $H_2$ at the exit 130 may be selected such that it is smaller than the diameter of the bead of the immunoassay so that the bead can be trapped within the channel 126 before reaching the exit 130 of the channel 126. In some instances, the height $H_2$ at the exit 130 may be between 0.5 μm and 8 μm.

A variety of exemplary dimensions of the microfluidic device 10, particularly for use with an immunoassay, are here provided. For example, the height $H_1$ at the entrance 128 of channel 126 may be about 4 μm and the height $H_2$ at the exit 130 of the channel 126 may be about 1 μm, such that the microfluidic device 10 is suitable for use with an immunoassay comprising beads having a diameter of no greater than 4 μm and no less than 1 μm. As another example, the height $H_1$ at the entrance 128 of channel 126 may be about 10 μm and the height $H_2$ at the exit 130 of the channel 126 may be about 5 μm, such that the microfluidic device 10 is suitable for use with an immunoassay comprising beads with a diameter no greater than 10 μm and no less than 5 μm. As yet another example, the height $H_1$ at the entrance 128 of channel 126 may be about 5 μm and the height $H_2$ at the exit 130 of the channel 126 may be about 2 μm, such that the microfluidic device 10 is suitable for use with an immunoassay comprising beads having a diameter of no greater than 5 μm and no less than 2 μm, or no greater than 4 μm and no less than 1 μm. The channel 126 may have a length $L_1$ that is equal to or greater than 2 cm.

In some embodiments within the scope of the present disclosure, the supply line 14 is pressurized, and the feeding pressure of the solution or assay is determined by the positive pressure settings of the supply line 14. In other embodiments within the scope of the present disclosure, a vacuum (not depicted) is attached to an outlet of the microfluidic device 10. In such embodiments, the feeding pressures of the solution or assay are created by a negative pressure at the outlet of the channel 126 and can be varied.

Figure 4:
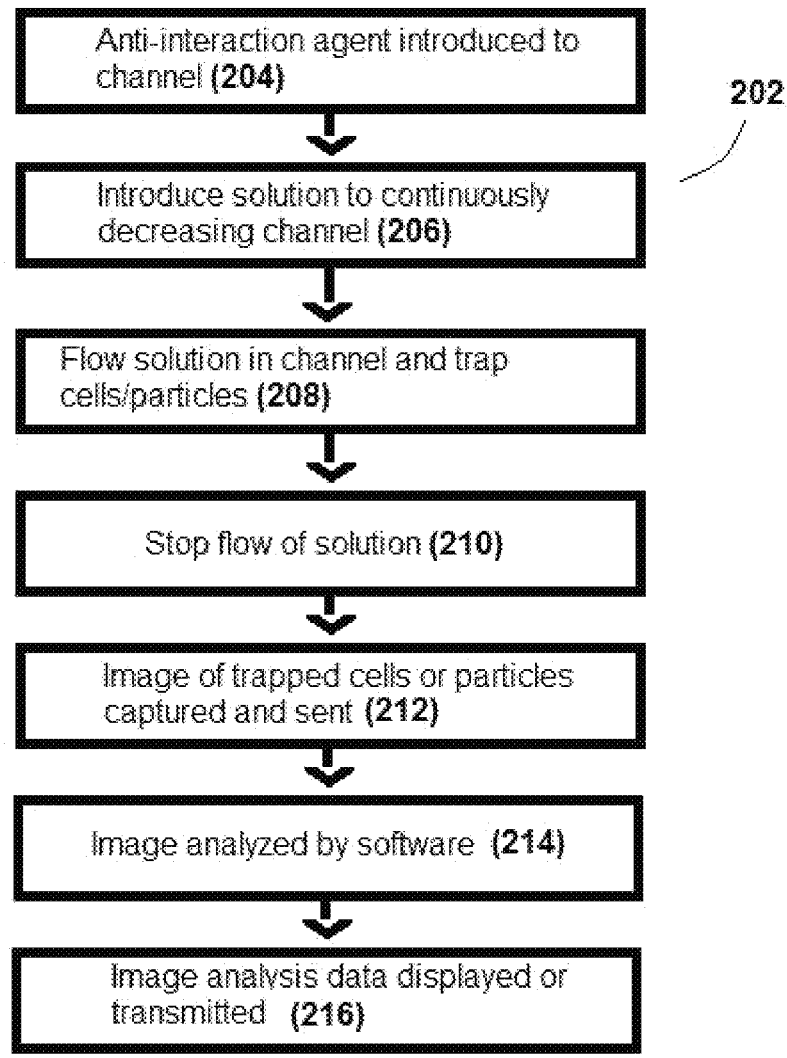
FIG. 4 is a flow chart illustrating a method of calculating the size and/or deformability of particles or cells via use of the microfluidic device.

FIG. 4 is a flow chart illustrating a method 202 of calculating the size and/or deformability of particles or cells via use of the microfluidic device system 2. At box 204, a an anti-interaction agent is introduced into a channel 126 of the microfluidic device 10 to prevent interaction between the walls of the channel 126 and any cells or particles later introduced to the channel 126. The anti-interaction agent may be a phosphate buffered solution (PBS) with 5% bovine serum albumin (BSA) solution. At box 206, a solution is introduced into the channel 126, the channel 126 (as described above) having an entrance with a higher height $H_1$ at the entrance 128 that decreases continuously to a lower height $H_2$ at the exit 130 of the channel. The solution may be a <1% V/V solution of the cells or particles being analyzed. At box 208, cells or particles of the solution are caused to flow within the channel 126 and become trapped in the channel 126 based on their size and/or deformability. In some instances, the cells or particles of the solution are caused to flow for 10 minutes at approximately 12 psi. At box 210, the flow of the solution is stopped. At box 212, an image of the trapped cells or particles is captured via a visual sensor 8 and sent to a data collection/readout device 4. In most instances, more than one image is captured with each image corresponding with a separate portion of the channel 126. At box 214, the image or images are analyzed by image software 6 to identify size and/or deformability information, such as the number of subsets of particles or cells having certain sizes or deformability characteristics and the relative size of such subsets. Optionally, at box 216, the image analysis data is either displayed or transmitted to the Internet or cloud storage.

Figure 5A:
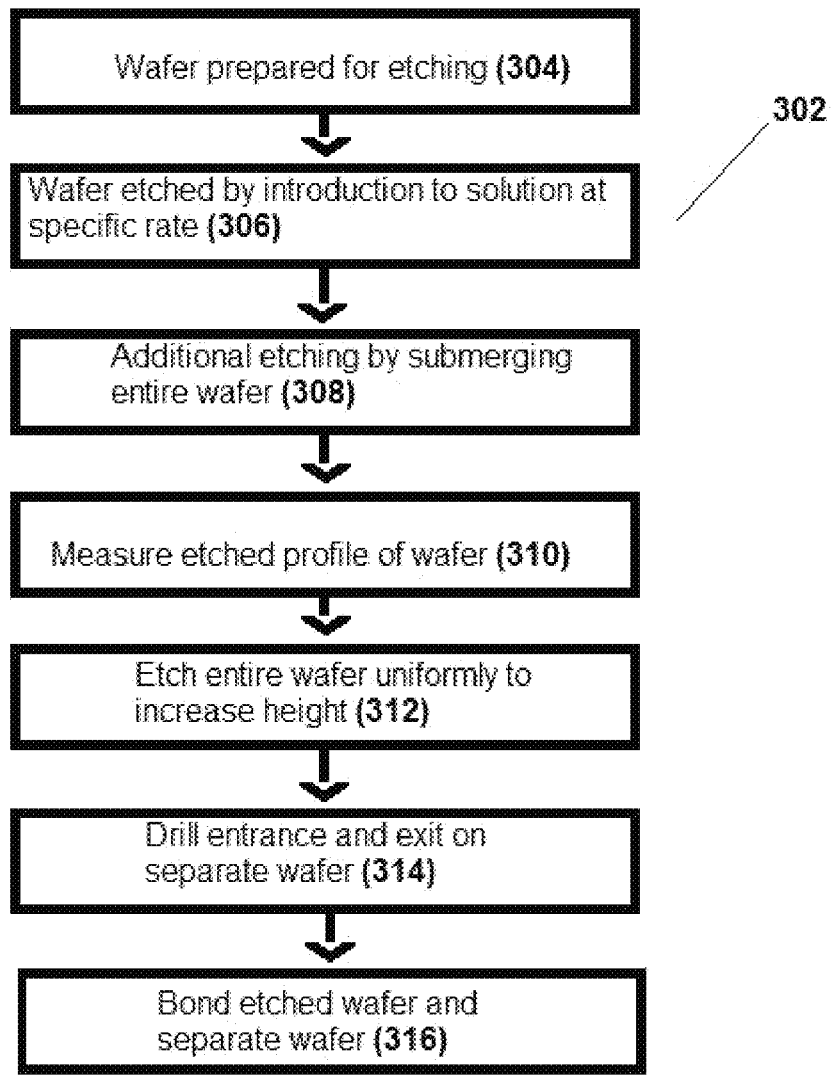
FIG. 5A is a flow chart illustrating a method of fabricating a microfluidic device having a channel that decreases continuously from the entrance to the channel to the exit of the channel.
Figure 5B:
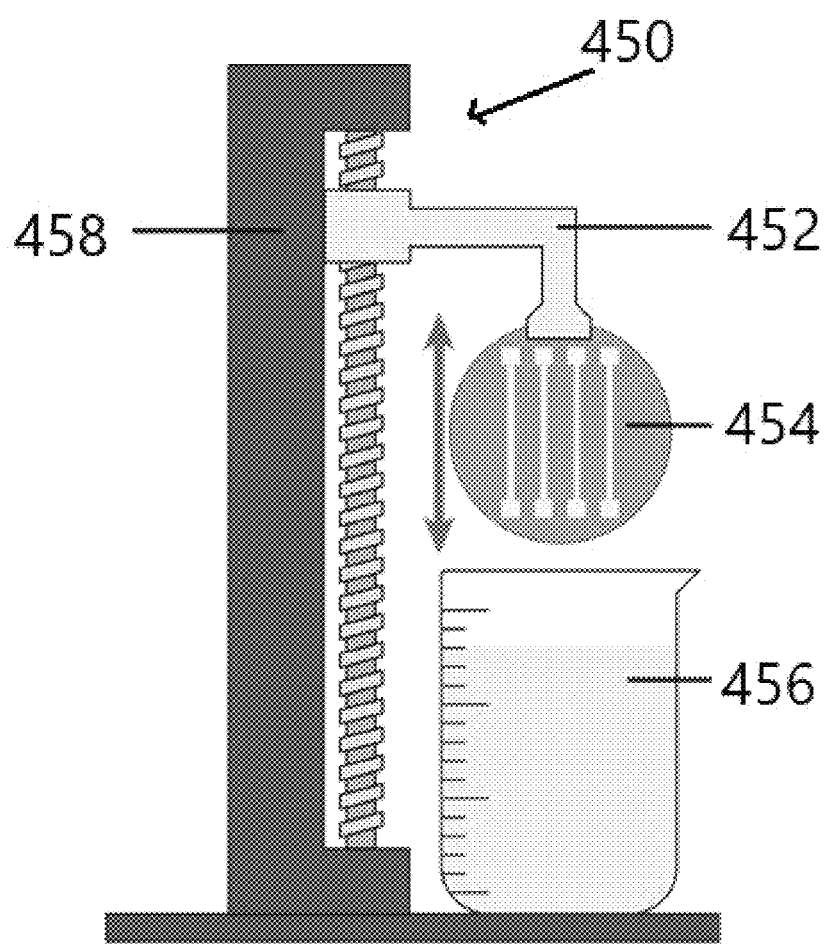
FIG. 5B illustrates equipment that may be used to fabricate a microfluidic device in accordance with the method illustrated in FIG. 4A.

FIG. 5A is a flow chart illustrating a method 302 of fabricating a microfluidic device 10. At box 304, a glass wafer is prepared for etching. Such preparation may include annealing the wafer, piranha cleaning the wafer, and depositing an etching mask on the wafer. At box 306, the glass wafer is etched by being introduced at a specific rate into an etching solution so that the end of the wafer introduced first is etched longer than the subsequent portions that go into the solution later. The specific rate may be a constant speed (resulting in linear profiles, such as those shown in FIG. 3A), may include an acceleration (resulting in quadratic profiles, such as those shown in FIG. 3B), and may include pauses to introduce incremental steps into a profile (also shown in FIG. 3A). Etching in this manner may be achieved by using a transverse mechanism of a syringe pump customized with a 3D-printed adapter designed to hold the wafer on one end and attached to a syringe pump on the other. Displacement of the pump may be varied by selecting different flow rates in order to allow for the creation of an etched profile having different slopes on the wafer. The wafer may have a target slope, and the specific rate that the wafer is introduced to the etching solution may be determined based on the target slope. The target slope may be determined based on the anticipated size or deformity of the cells or particles in the solution to be studied using the microfluidic device system 2. Alternately, FIG. 5B shows an arrangement 450 where a 3D printed adapter 452 holds a wafer 454 during introduction to an etching solution 456, the 3D printed adapter 452 being secured on a linear screw assembly 458 having a linear screw actuator that may be programmed to properly etch the wafer 454. Returning to FIG. 5A, at box 308, additional etching to form the smallest heights on the wafer may be performed by preventing a portion of the wafer from being etched at box 306 and then submerging the entire wafer into an etching solution, such as HF, using a standard wafer holder. At box 310, the etched profile of the glass wafer may be measured, such as by using a surface profilometer. At box 312, the entire wafer may be etched uniformly to increase height. At box 414, an entrance and an exit to the microfluidic device 10 may be drilled on a separate glass wafer. At box 416, the etched glass wafer and the separate glass wafer may be bonded together.

Microfluidic Assay

The disclosure provides a point-of-care microfluidic assay (e.g., an immunoassay) for detection and/or diagnosis of various conditions, such as traumatic brain injury (TBI). For example, the assay can be an immunoassay that can be used for the quantification of GFAP concentrations in cerebrospinal fluid (CSF), serum, and whole blood. The assay can be used in connection with the microfluidic device described herein. Fluorescence quantification can be carried out using a reusable optics module that correlates the amount of fluorescence with the concentration of a target protein, for example, GFAP. The assay allows the device to capture beads with a continuum of diameters, and provides for the measurement of, for example, multiple TBI biomarkers in a single patient sample (provided that a different sized bead is used for each biomarker assay). The assay and corresponding device are designed such that it can fit in a pocket, enabling its use in the field, pre-hospital, and hospital settings.

Solution Comprising Target Protein

The assay of the disclosure includes a solution comprising a target protein. In embodiments, the solution comprising the target protein comprises cerebral spinal fluid (CSF), whole blood, blood serum, or a mixture thereof. In some embodiments, the solution comprises CSF. In some embodiments, the solution comprises whole blood. In some embodiments, the solution comprises blood serum.

The target protein can be any protein of interest. For example, the target protein can be associated with a TBI. In embodiments, the target protein comprises GFAP, NF-L, UCH-L1, S-100B, IL-6, or a mixture thereof. In some embodiments, the target protein comprises GFAP. In embodiments, the target protein comprises IL-6. In embodiments, the assay is capable of detecting the target protein at a concentration of 0.01 ng/mL to 50 ng/mL.

First Complex

The assay of the disclosure further includes a first complex. The first complex comprises a bead, wherein the bead has a diameter and a surface. The surface of the bead is substantially coated with a first molecule. As used herein, "substantially coated with a first molecule" means that at least about 50%, 60%, 70%, 75%, 80%, 90% and/or up to about 60%, 70%, 80%, 90%, 95%, 99%, 99.5%, 99.9%, or 100% of the surface of the bead is coated with a first molecule. The first molecule can provide a coating for the bead via any suitable intermolecular or intramolecular interaction(s), for example, via covalent bond(s), ionic bond(s), hydrophobic interactions, and/or hydrogen bonding. For example, in some cases, the first molecule can be an antibody that coats the bead via an affinity of protein G for IgG (e.g., a first antibody). As provided herein, the bead has a diameter. The bead may have a diameter of at least about 1, 2, 3, 4, 5, 6, and/or up to about 4, 5, 6, 7, 8, 9 or 10 µm, for example, 1 µm to 10 µm, 3 µm to 10 µm, or 5 µm to 7 µm. In embodiments, the bead has a diameter of 1 µm to 10 µm. In embodiments, the bead is magnetic. In embodiments, the bead comprises latex. In embodiments, the bead is photobleached. That is, in embodiments, the bead is prepared such that it does not autofluoresce.

As provided herein, the first complex comprises a first molecule. The first molecule can be any molecule suitable for binding to the target protein, such as DNA, RNA, or an antibody. As would be appreciated by the person of ordinary skill in the art, the particular selection of the first molecule will depend on the particular target protein(s) that are being detected by the assay. In embodiments, the first molecule is DNA or a fragment thereof. In embodiments, the first molecule is RNA or a fragment thereof. In embodiments, the first molecule is an antibody. In embodiments, the first antibody comprises a monoclonal antibody or a polyclonal antibody. In some embodiments, the first molecule is a monoclonal antibody. In embodiments, the first molecule is a GFAP monoclonal antibody.

The assay can include any ratio of bead to first molecule that would be suitable to detect the target protein. In embodiments, the first complex includes a bead:first molecule ratio of about $10:10^7$ to about $10:10^5$. For example, in embodiments, the bead:first molecule (e.g., antibody) ratio is about $67:2 \times 10^7$.

Second Complex

As provided herein, the assay further includes a second complex. The second complex comprises a second molecule and a quantum dot. As with the first molecule, and as would be appreciated by the person of ordinary skill in the art, the second molecule can be particularly selected depending on the particular target protein being evaluated by the assay. For example, the second molecule can be any molecule suitable for binding to the target protein, such as DNA, RNA, or an antibody. In embodiments, the second molecule is DNA or a fragment thereof. In embodiments, the second molecule is RNA or a fragment thereof. In embodiments, the second molecule is an antibody. In embodiments, the second molecule comprises a monoclonal or a polyclonal antibody. In some embodiments, the second molecule is a polyclonal antibody. In embodiments, the second molecule is a GFAP polyclonal antibody.

Without intending to be bound by theory, it is believed that the sensitivity of the assay is, in part, dependent on the selection of the first and second molecules relative to the target protein. For example, in embodiments, the first molecule and the second molecule each recognize at least one unique site on the target protein. Furthermore, the first and/or second molecule should not bind to other species (i.e., other than the target protein) that may be present in the solution. In some cases, the solution(s) may be spiked with interferents to inhibit and/or mitigate the binding of the first and/or second molecule to species other than the target protein. Suitable interferents include, but are not limited to, $Ca^{2+}$, $K^+$, $Mg^{2+}$, glucose, glycine, albumin, and cholesterol esterase.

The second complex further includes a quantum dot. As would be understood by a person of ordinary skill in the art, a quantum dot is a small semiconductor particle having a diameter of a few nanometers. Quantum dots have optical and electrical properties and can be illuminated via UV light. Examples of suitable quantum dots for use in the assays of the disclosure include, but are not limited to QDOT™ 525, QDOT™ 545, QDOT™ 565, QDOT™ 585, QDOT™ 605, QDOT™ 625, QDOT™ 655, QDOT™ 705, and QDOT™ 800. Quantum dots can also be fabricated in a lab according to methods generally known in the art. In embodiments, the quantum dot comprises a conjugate comprising streptavidin and a fluorescent label. In embodiments, the concentration of the quantum dot is at least about 0.1 nM, 0.5 nM, 1 nM, 5 nM, 10 nM, 25 nM, 50 nM, 100 nM and/or up to about 50 nM, 100 nM, 250 nM, 500 nM, 750 nM, or 1 µM. For example, in embodiments, the concentration of the quantum dot is 0.1 nM to 1 µM.

The second complex includes the second molecule which is associated with the quantum dot. As used herein, the term "associated with" means that the second molecule can be entangled, embedded, incorporated, bound to the surface, or otherwise associated with the quantum dot, via any suitable intermolecular or intramolecular interaction. In embodiments, the second molecule is directly associated with the quantum dot. That is, in embodiments, the second complex is free of a linker compound.

In embodiments, the second complex further includes a linker compound, such as a protein. The linker compound can be used to bind the second molecule to the quantum dot. The linker compound can associate with each of the second molecule and the quantum dot via any suitable intermolecular or intramolecular interaction(s). In embodiments, the linker compound comprises biotin, polyethylene glycol (PEG), protein G, protein A, a carboxyl group, or an epoxy group. In embodiments, the linker compound comprises biotin. In embodiments, the linker compound comprises PEG. In embodiments, the linker compound comprises protein G. In embodiments, the linker compound comprises protein A. In embodiments, the linker compound comprises a carboxyl group. In embodiments, the linker compound comprises an epoxy group.

Multiplex

Figure 6:
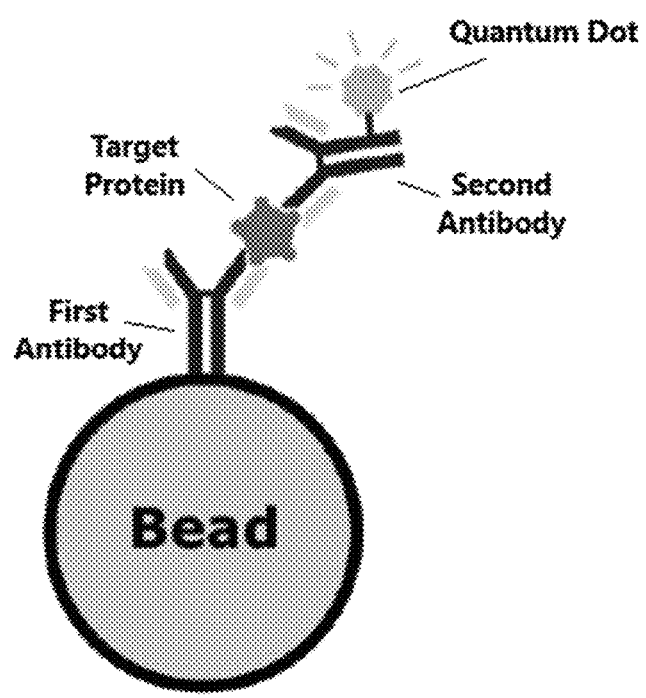
FIG. 6 illustrates a multiplex according to the disclosure.

The assay functions through the interactions between the solution comprising the target protein, the first complex, and the second complex. In particular, the assay can provide, for example, a multiplex, or "sandwich," in which the first molecule (i.e., coated on the bead), and the second molecule (i.e., associated with the quantum dot with or without a linker compound) can interact with the target protein in the solution. That is, when exposed to the target protein, the first molecule and the second molecule interact with the target protein to form a multiplex on the surface of the bead. One example of this multiplex, using an antibody as each of the first and the second molecule, is illustrated in FIG. 6.

Methods of Use of the Microfluidic Assay

Figure 7:
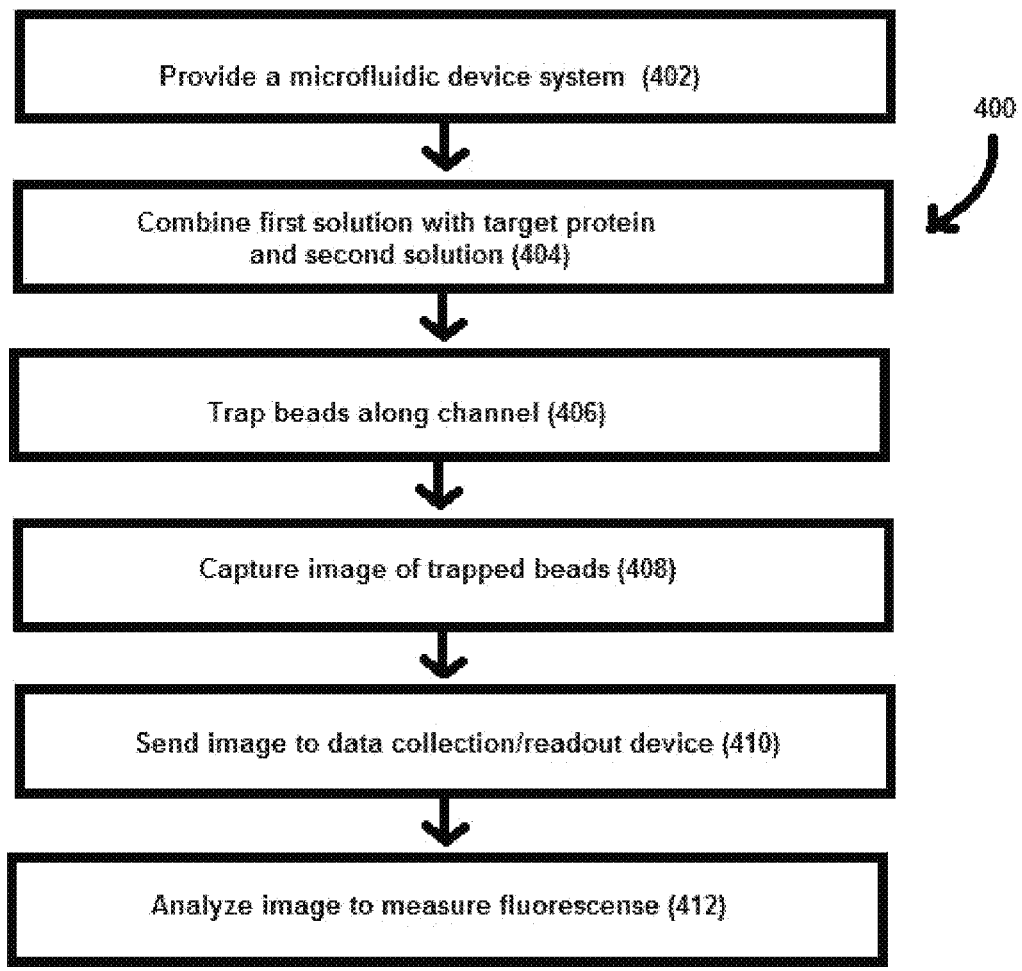
FIG. 7 is a flow chart illustrating a method of using a microfluidic assay in a microfluidic device according to the disclosure.

A method 400 of using the assay described herein with the microfluidic device 10 is shown in FIG. 7. At box 402, the method 400 includes providing a microfluidic device, such as microfluidic device 10, having a channel 126 having a height $H_1$ that is greater at an entrance to the channel 126 than a height $H_2$ at an exit of the channel 126, the channel 126 decreasing in height from the entrance 128 to the exit 130. At box 404, the method 400 includes combining a first solution with a target protein and a second solution. The first solution comprises a plurality of beads, each bead having a diameter and a surface substantially coated with a first molecule, as described herein. The second solution comprises a second molecule associated with a quantum dot. As a result of the combining step at box 404, the first molecule and the second molecule associate with the target protein to form a multiplex on the surface of each of the plurality of beads. At box 406, the method 400 includes trapping each bead of the plurality of beads along the channel 126 based on the diameter of the bead. At box 408, the method 400 includes capturing an image of the trapped plurality of beads, for example by a visual sensor 8. At box 410, the method 400 includes sending the image to a data collection/readout device 4. At box 412, the method 400 includes analyzing the image using image software 6 to measure the fluorescence of the multiplex on the surface of at least one of the trapped beads located at one or more locations along the channel 126.

The bead and the first molecule can be selected as described herein, and the molecule can interact with the surface of the bead via any of the intermolecular or intramolecular interactions described herein. The first solution (i.e., comprising the plurality of beads and the first molecule) can also include a solvent, such as phosphate-buffered saline (PBS). The first solution can also include bovine serum albumin (BSA), in an amount ranging from about 1% to about 10%, or about 3% to about 7% by weight of the first solution. In embodiments, BSA is present in an amount of about 6% by weight of the first solution.

Each of the second molecule and quantum dot can be selected as described herein. In embodiments, the second solution can further include a linker compound, such as those described herein, such that the linker compound binds the second molecule to the quantum dot. In embodiments, the linker compound comprises biotin, polyethylene glycol (PEG), or a combination thereof. The second solution (i.e., comprising the second molecule and the quantum dot) can also include a solvent, such as phosphate-buffered saline (PBS). The second solution can also include bovine serum albumin (BSA), in an amount ranging from about 1% to about 10%, or about 3% to about 7% by weight of the second solution. In embodiments, BSA is present in an amount of about 6% by weight of the second solution.

The target protein can be selected as described herein, and can be present in a solution comprising cerebral spinal fluid (CSF), whole blood, blood serum, or a mixture thereof. The solution comprising the target protein can be an undiluted solution (e.g., blood drawn directly from the patient), or it can be further diluted to a concentration appropriate for use in the assay.

The order of combination and injection into the device is not particularly limited. In embodiments, the combining of the first solution with the target protein and the second solution occurs in the channel.

For example, in embodiments, the first solution is combined with the target protein prior to injecting into the channel of the microfluidic device, and the second solution is thereafter directly injected into the channel of the device. For example, the first solution and the target protein can be combined prior to injection, such that upon injection to the device, the target protein is already associated with the first molecule that is coated on the surface of the bead via the interactions between the target protein and the first molecule. Thereafter, the second solution (comprising the second molecule and the quantum dot) can be injected into the device, thereby forming the multiplex within the device (e.g., at the location of the target protein/first complex via the interactions between the second molecule and the target protein).

In embodiments, the second solution is combined with the target protein prior to injecting into the channel of the microfluidic device. In such embodiments, the first solution can be injected into the device (thereby trapping the beads and first molecule within the channel according to height of the channel and diameter of the bead), and the mixture comprising the target protein and second solution (e.g., the target protein being associated with the second molecule) can be subsequently injected into the device, such that the multiplex is formed within the device (e.g., at the location of the trapped beads via the interactions between the target protein and the first molecule).

In embodiments, each of the first solution, the target protein, and the second solution are individually injected into the device. In such embodiments, the first solution is injected to the device, thereby trapping the beads and first molecule within the device. Thereafter, the target protein (or solution comprising the target protein) can be injected thereby trapping the target protein at the location of the trapped beads via the interactions between the first molecule and the target protein. Thereafter, the second solution (comprising the second molecule associated with the quantum dot) can be added to the device such that the multiplex is formed within the device (e.g., at the location of the trapped beads/target protein via the interactions between the second molecule and the target protein).

In embodiments, the first solution, target protein, and second solution can be combined prior to injection into the device. That is, the multiplex can be formed external to the device and subsequently injected into the device.

This image of the trapped beads can be obtained, for example, via fluorescence spectroscopy, wherein the quantum dot will fluoresce at the location at which the multiplex is trapped along the length of the channel. In embodiments, the capturing of the image includes capturing a brightfield image and capturing a fluorescence image, and analyzing the image using image software includes comparing the brightfield image with the fluorscense image. Without intending to be bound by theory, the degree of fluorescence can be directly related to the concentration of the target protein within the sample.

In embodiments, the method further includes priming the channel of the device with a priming solution prior to trapping each multiplex along the channel. In embodiments, the priming solution comprises BSA. In embodiments, the concentration of the BSA in the priming solution is at least about 1, 3, 5, 7% and/or up to about 5, 7, 9, or 10% by weight, based on the total weight of the priming solution.

As would be appreciated by the person of ordinary skill in the art, the use of the assay, taken alone, as well as with the microfluidic device, can be applicable to detecting and measuring not only a single target protein, but also a multitude of target proteins. In embodiments, the method comprises a second target protein. For example, the assay and the use of the assay with the microfluidic device can be modified in order to trap two or more multiplexes along the length of the channel of the device. Provided that the size of the bead and the selection of the first and second molecules are unique for a particular target protein, the assay, and method of use with the microfluidic device, can be used to detect more than one protein in a given sample.

Kit

The disclosure further provides a kit for determining the concentration of a target protein in a solution comprising the microfluidic assay as described herein, and a microfluidic device system 2 as described herein having a channel 126 having a height $H_1$ that is greater at an entrance 128 to the channel 126 than a height $H_2$ at an exit 130 of the channel 126, the channel 126 decreasing in height from the entrance 128 to the exit 130.

It is understood that while the disclosure is read in conjunction with the detailed description thereof, the foregoing description and following examples are intended to illustrate and not limit the scope of the disclosure, which is defined by the scope of the appended claims. Other aspects, advantages, and modifications are within the scope of the following claims.

EXAMPLES

Example 1

Wafer Preparation

BOROFLOAT® wafers were annealed at 560° C. for one hour (TEMPRESS S6T1) and then piranha cleaned. To make the etching mask, a 200 Å layer of chromium and a 2000 Å gold were deposited on the clean wafers (E-Beam Evaporator). A 3 µm layer of S1827 positive photoresist (MICROCHEM) was spin coated and exposed using a Mask aligner. The development was carried out using AZ 726, TFA gold etchant, and CR-1020 chrome etchant (TRANSENE). The photoresist was left in the etching step to further protect the gold/chromium layers. This allowed for a cleaner etch. The glass was etched with a hydrofluoric acid (HF) solutions with concentrations ranging from 49% to 15%. After the etching, the photoresist was removed with acetone and isopropyl alcohol, while the gold and chromium layers were removed with their corresponding etchants.

The inlet and outlets were drilled on a separate wafer using electrochemical drilling with sodium hydroxide or a Tormach PCNC 440. The etched and drilled wafers were ionic and organic cleaned before depositing a 2 µm layer of parylene (SCS PDS 2035CR). The wafers were bonded using the SB-6E to create the devices.

Etching Procedure

To create a variable height device, the wafers were non-uniformly exposed to HF. To do this the wafers were slowly introduced at a specific rate into the HF solution so that the end introduced first was etched longer than the end that went into the solution later. This was accomplished by using the transverse mechanism of a syringe pump customized with a 3D-printed adapter that was specially designed to hold the wafer on one end and attach to a syringe pump (HARVARD APPARATUS, PHD 2000) on the other. The displacement of the pump was varied by selecting different flow rates, which allowed for the creation of different slopes. After the wafer achieved the desired etching, the pump head was lifted away from the beaker and rinsed with deionized water for at least 5 minutes.

To create the smallest heights on the wafer, only ~90% of the wafer was introduced into the solution. The wafer was taken out of the liquid and the 3D-printed adapter and rinsed with DI water for 5 minutes. To etch the final 10% of the channel (~5 mm), the entire wafer was submerged into the HF using a standard wafer holder. With the wafer holder, the final exposure to HF was more controlled and allowed for the etching of heights of just 1 µm or below.

Figure 8:
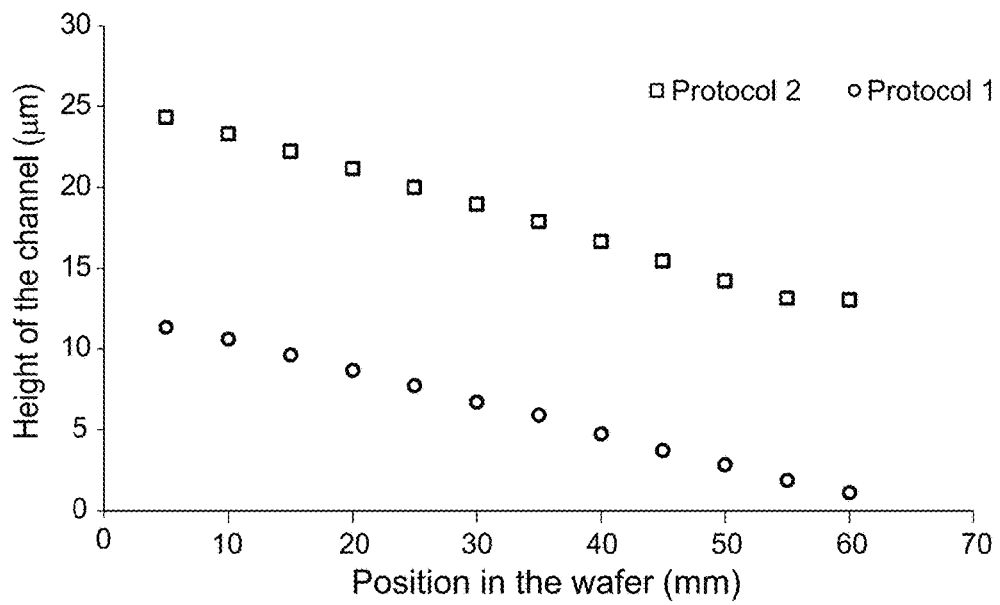
FIG. 8 is a graph of the height of the channel of a microfluidic device according to the disclosure at various positions in the wafer.

The resulting etched profiles were measured with a surface profilometer and are shown in FIG. 8. The height of the channel in micrometers is shown as a function of the location in the wafer. The transverse speed of the pump was 30 mm/min in HF 49%. For protocol 2, the first part of the process was identical to protocol 1. After creating the sloped channel, the entire wafer was etched uniformly in HF to increase the height.

Example 2

Three different sizes of particles were introduced into the same channel starting from the biggest particle to the smallest. The particles were fluorescent particles with different colors, so that only one size of particle was visible when using a specific optical filter. The particles were purchased from SPHEROTEC with the following characteristics: sky blue particles (MFP-2070-5 1.7-2.2 µm), pink particles (TFP-5058-5 5.0-5.9 µm), yellow particles (TFP-7052-5 7.0-7.9 µm). A NIKON Eclipse inverted microscope with fluorescent capabilities was used for the imaging.

Figure 9:
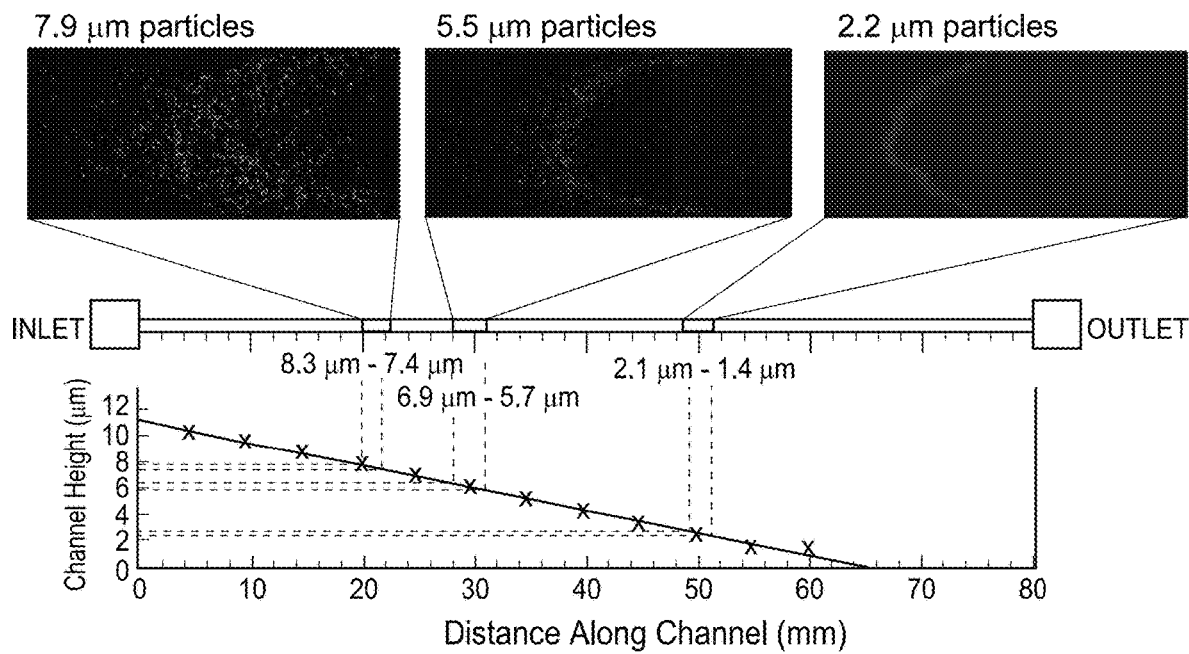
FIG. 9 shows fluorescence images of particles having different sizes after being introduced to a microfluidic device according to the disclosure.

As shown in FIG. 9, the particles stopped at different locations in the channel according to their size (from left to right: 7.9 µm particles, 5.5 µm particles, and 2.2 µm particles).

Example 3

Figure 10:
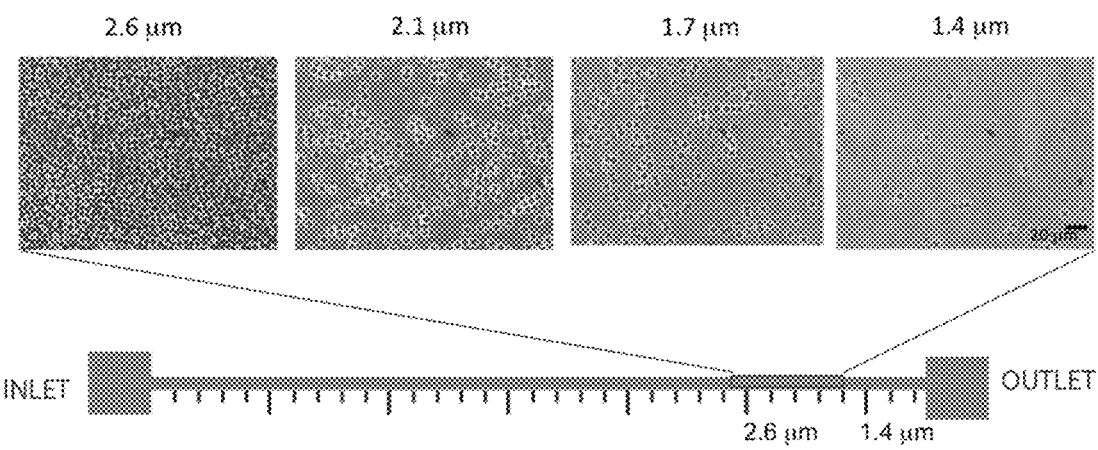
FIG. 10 shows images of human red blood cells (RBCs) after being introduced to a microfluidic device according to the disclosure.

Healthy red blood cells were introduced into the device. Whole blood was centrifuged and washed with phosphate buffered solution 1x with 5% bovine serum albumin. The same solution was infused into the channel for 30 minutes to minimize interactions with the walls. The red blood cells where diluted to approximately 1% hematocrit and flowed for 10 minutes at a pressure of 12 psi. The results of the red blood cells from a healthy human passing through the variable height channel are shown in FIG. 10.

As the cells travel the portion of the channel having a height between 2.6 and 1.4 µm, they were trapped according to their ability to deform. Only a few made it to the portion of the channel having a 1.4 µm height.

Figure 11:
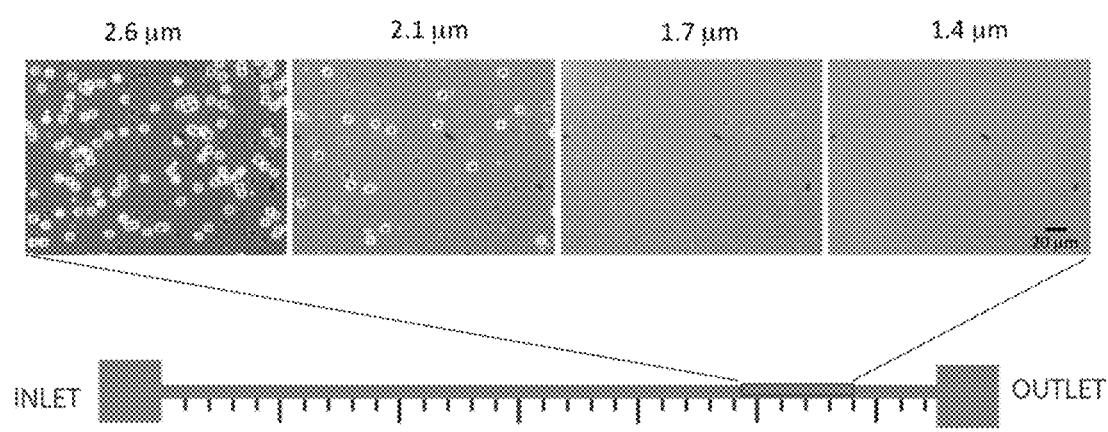
FIG. 11 shows images of human RBCs treated with glutaraldehyde after being introduced to a microfluidic device according to the disclosure.

In order to induce a reduction in deformability, the red blood cells were incubated for one hour in a solution of 0.02% of glutaraldehyde. These treated cells were flowed under the same parameters of concentration, pressure, and time into a new channel. The results are shown in FIG. 11. By comparing the results in FIG. 10 with the results in FIG. 11, a difference in the stopping point between healthy and treated red blood cells is apparent. Treated cells do not pass the 2.1 µm section of the channel. In fact, few cells make it to the 2.6 µm section with cells stopping at even higher heights.

Example 4

Figure 12:
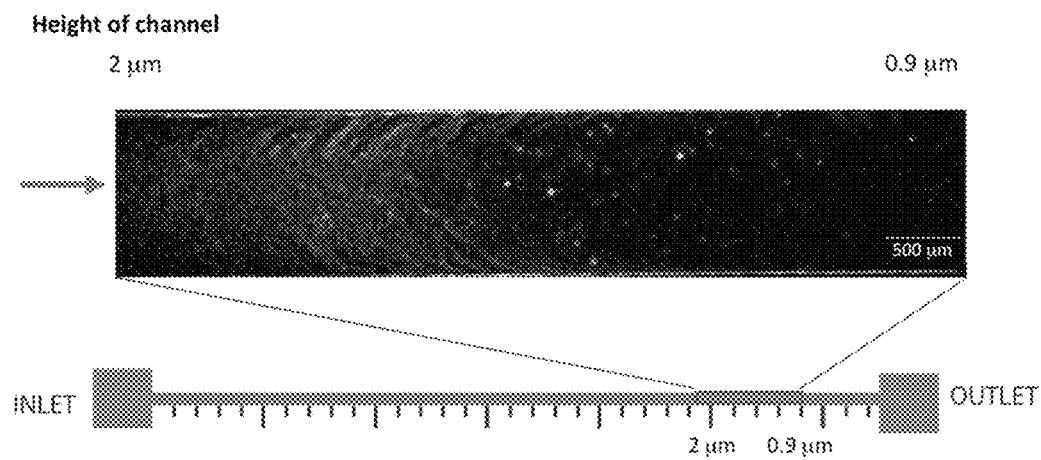
FIG. 12 shows an image of swine RBCs after being introduced to a microfluidic device according to the disclosure.

The continuous nature of the channel can be used to study subpopulations of cells and particles. For instance, in FIG. 12, healthy red blood cells from swine can be seen to form different rings that might represent different subpopulations of deformability. Even in healthy cells, a range of deformability is present due to the different age and properties of the cells. The ability to analyze many cells at once is a unique property of the microfluidic device of the present disclosure.

Example 5

Figure 13:
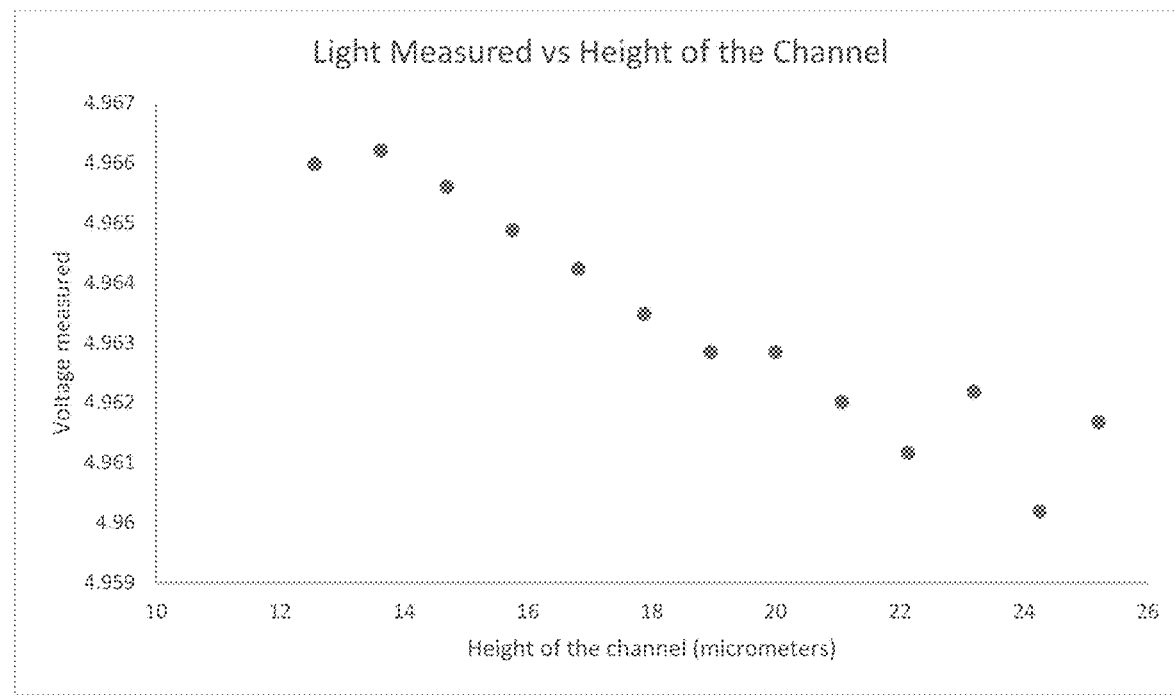
FIG. 13 is a graph of the amount of light measured as a function of the height of the channel of a microfluidic device according to the disclosure.

Based on the Beers-Lambert law, the light absorbed by a liquid is a function of the concentration, the path length and the absorptivity of the liquid. Following this principle, at different positions in the channel the absorbed light will be a function of the thickness of the liquid (the height of the channel). To test this principle, food colorant was introduced into a channel with thickness from 24 to 13 micrometers and the voltage was measured resulting at different positions. A correlation was observed in FIG. 13 with more light being absorbed (less voltage being measured) at the thickest part of the wafer. This principle will allow the channel of the microfluidic device to be used as a spectrophotometer. Applications can include the measurement of the concentration of different solutions (including blood, i.e. hematocrit content), and any other solution.

Comparative Example 6—Commercial Assay

The following example uses a commercially available immunoassay with the microfluidic device to detect GFAP in a sample. The commercially available assay, from QUANTERIX®, is a typical ELISA assay where an enzyme is used to generate a fluorescent product that is not directly tied to the bead. The QUANTERIX assay is designed to be used with Simoa devices that trap single beads in femtoliter sized wells. The wells trap the fluorescent product and prevent it from diffusing away from the beads. The QUANTERIX analyzer carries out all of the assay steps and then counts the number of wells that are fluorescing or if all of the wells are filled, quantifies the overall fluorescence intensity. The number of fluorescent wells or the overall fluorescence intensity are related to how much GFAP was in the sample. The assay range of the commercially available assay is 0-4,000 pg/mL in serum and plasma. The assay can also accommodate diluted CSF samples.

Reagent Preparation

Bead Reagent

The beads, having a GFAP antibody coupled thereto, were washed by adding 1 mL of Discovery Bead Diluent (QUANTERIX®) to 1 vial of bead stock. The vial was inverted to mix. Using a magnetic stand, the beads were captured and the diluent was aspirated. The beads were then resuspended in 1 mL of Discovery Bead Diluent and vortexed to mix. The resuspended beads were combined with 4 mL of Discovery Bead Diluent to dilute to the appropriate concentration in an amber reagent bottle and vortexed to mix.

Detector Reagent

A 470 µL aliquot of Discovery Detector Diluent (QUANTERIX®) was added to 30 µL of GFAP Detector Stock (QUANTERIX®) (comprising a GFAP antibody coupled with biotin) and vortexed to mix.

SBG Reagent

A 1.2 mL aliquot of Discovery SBG Diluent (QUANTERIX®) was added to 1.51 µL of Discovery SBG Concentrate (QUANTERIX®) (comprising the enzyme) and vortexed to mix.

1×PBS Solution

A 10×PBS solution was diluted to 1× by combining 2 mL of 10×PBS with 18 mL of DI water and vortexed to mix.

1×PBS+0.1% Triton X-100

The 1×PBS was combined with 20 µL of Triton X-100 and vortexed to mix.

Samples Tested
1) Control (1×PBS+0.1% BSA)
2) 3.45 µg/mL GFAP in 1×PBS+0.1% BSA
3) 6.9 µg/mL GFAP in 1×PBS+0.1% BSA Reaction Protocol A 100 µL aliquot of the Bead Reagent was added to the process vial, followed by the addition of 152 µL of the sample (comprising the GFAP). A 100 µL aliquot of the Detector Reagent was added, followed by addition of 100 µL of the SBG Reagent. The vial was vortexed to mix all of the solutions, and incubated for 35 minutes at room temperature. The beads were washed seven times with 1×PBS+0.1% Triton X-100 by using a magnetic stand to capture the beads, and the supernatant was aspirated. The beads were washed once with 1×PBS by using a magnetic stand to capture the beads, and the supernatant was aspirated. A 200 µL aliquot of RGP Reagent, comprising the substrate that the enzyme converts to a fluorescent product, was added to the dry beads and vortexed to mix.

Device Preparation

The microfluidic device was primed with a solution of 5 wt % BSA in RGP Reagent for 30 minutes prior to use. The beads and RGP reagent mixture was introduced into the device using a pressurized microcentrifuge tube. The pressure was adjusted until the beads flowed through the variable height channel of the device and remained trapped. Imaging was initiated once a line of the beads became visible in the channel with the naked eye.

Fluorescence Imaging

Images of the trapped beads were captured using an inverted NIKON Eclipse Ti and an EXi Blue Camera. The camera gain was set to 9 and the exposure time to 3000 ms to capture the fluorescence images. A 49305 filter cube from Chroma Technologies was used to capture fluorescence images. Brightfield images of the trapped beads for comparison were captured. The color of the captured grayscale fluorescence images were changed to Orange Hot by changing the LUT in Fiji.

Results

Figure 14:
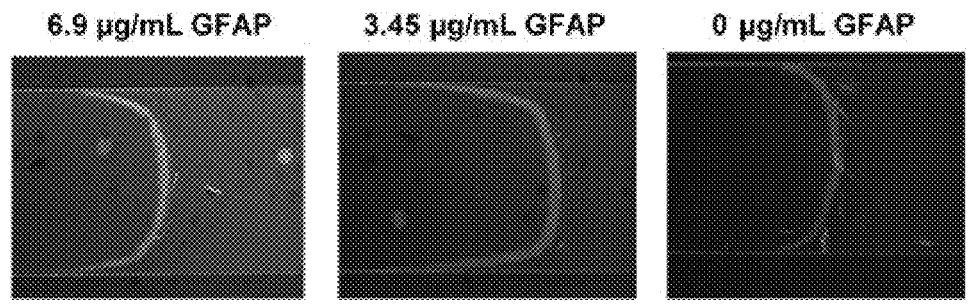
FIG. 14 shows fluorescence images of a commercially available immunoassay used in a microfluidic device disclosed herein.

As shown in FIG. 14, the fluorescence intensity decreased with decreasing GFAP concentration. However, the tested concentrations were not reflective of physiological conditions. The comparative assay was not sensitive enough when used with the microfluidic device to detect concentrations of GFAP that would be present in cerebrospinal fluid (CSF) (ng/mL) or in serum (pg/mL).

Example 7—Evaluation of Binding of Quantum Dot to Bead Surface

Reagent Preparation

Dynabeads™ M-280 Streptavidin Beads were obtained and resuspended in a vial by vortexing for 30 seconds. A 50 µL sample of the beads were transferred to a tube, and 1 mL of 1×PBS was added. The mixture was vortexed for 5 seconds to mix. The tube was placed on a magnet for 1 minute and the supernatant was discarded. The beads were resuspended in 500 µL of 1×PBS.

Five concentrations of quantum dot (QDOT® 585) solutions were prepared (20 nM, 10 nM, 5 nM, 2.5 nM, and 0 nM). For the 20 nM solution, 2 µL of QDOT® 585 stock was combined with 100 µL of 1×PBS+6% BSA and vortexed to mix. For the 10 nM solution, 50 µL of the 20 nM solution and 50 µL of the 1×PBS+6% BSA were combined and vortexed to mix. For the 5 nM solution, 50 µL of the 10 nM solution and 50 µL of the 1×PBS+6% BSA were combined and vortexed to mix. For the 2.5 nM solution, 50 µL of the 5 nM solution and 50 µL of the 1×PBS+6% BSA were combined and vortexed to mix. The 0 nM solution included 100 µL of 1×PBS+6% BSA.

A biotin-PEG-biotin solution was prepared by adding 14 mg of biotin-PEG-biotin M (MW 600, Creative PEGWorks) to 14 mL of DI water to create a 1 mg/ml solution.

The following experimental conditions were tested:
1) Beads only (negative control)
2) Quantum dots only (positive control)
3) Beads and quantum dots (negative control)
4) Beads, biotin-PEG-biotin linker, 20 nM quantum dot solution
5) Beads, biotin-PEG-biotin linker, 10 nM quantum dot solution
6) Beads, biotin-PEG-biotin linker, 5 nM quantum dot solution
7) Beads, biotin-PEG-biotin linker, 2.5 nM quantum dot solution
8) Beads, biotin-PEG-biotin linker, 0 nM quantum dot solution (negative control)

Reaction Protocol

A 100 µL sample of the bead solution was combined with 50 µL of sample (either DI water or biotin-PEG-biotin solution) and incubated at room temperature for 30 minutes. The beads were separated on a magnet for 3 minutes. The beads were washed 5 times with 500 µL 1×PBS+0.1% BSA by using a magnetic stand to capture the beads, and the supernatant was aspirated. A 50 µL aliquot of the appropriate quantum dot solution was added and incubated for 30 minutes at room temperature. The sample was washed three times for 5 minutes in 1×PBS by using a magnetic stand to capture the beads, and the supernatant was aspirated. The beads were resuspended in 500 µL of 1×PBS.

Microscope Slide Preparation and Fluorescence Imaging

A 30 µL sample of the resuspended bead solution was pipetted onto a microscope slide and a coverslip was placed on top.

Images of the solution on the microscope slides were captured using an inverted NIKON Eclipse Ti and an EXi Blue Camera, ensuring that the camera gain and exposure time were the same for all images. Using a 39104 filter cube from Chroma technologies, fluorescent images were captured. Brightfield images of the beads for comparison with the fluorescent images were also captured. The color of the captured grayscale fluorescence images were changed to Orange Hot by changing the LUT in Fiji.

Results

Figure 15:
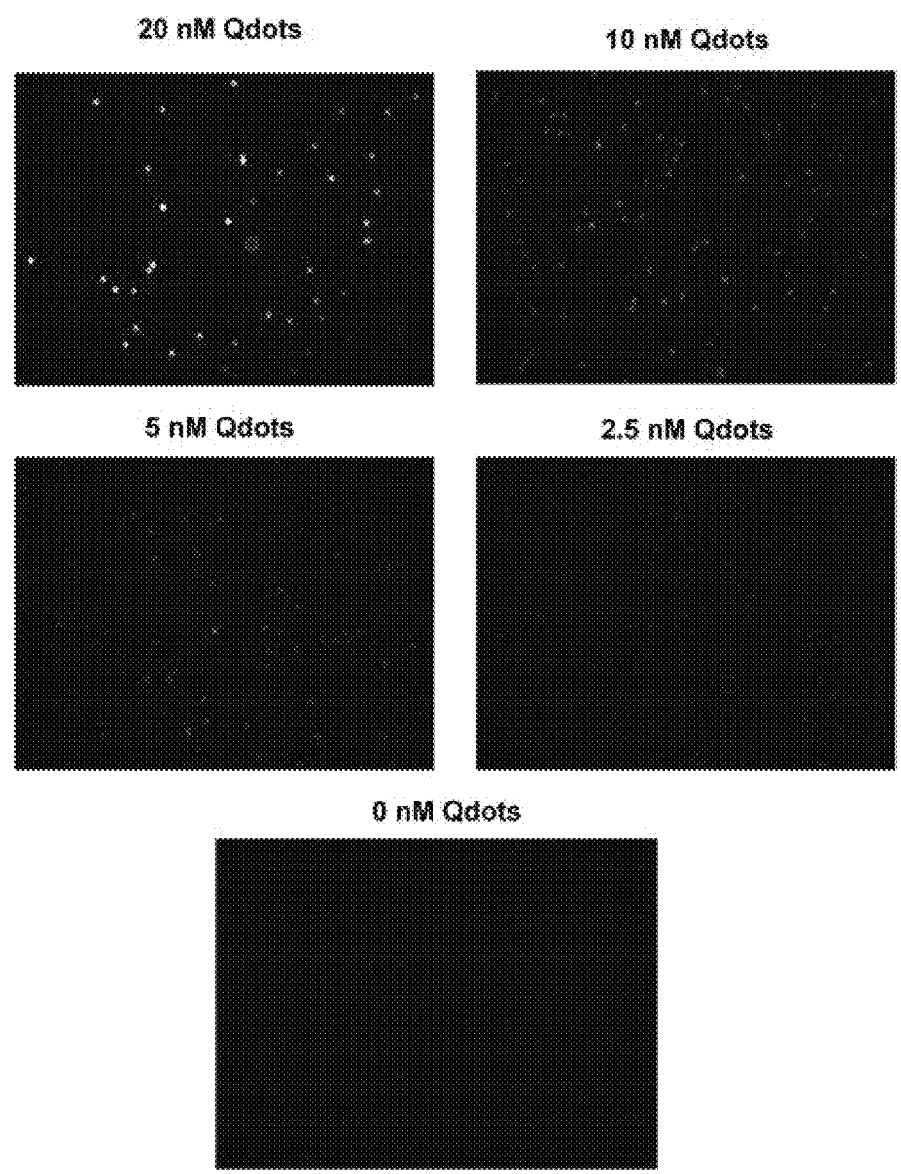
FIG. 15 shows fluorescence images of a quantum dot associated with the surface of a bead as described herein.

As shown in FIG. 15, the results of Example 7 demonstrated that the quantum dots localized to the surface of the beads. Furthermore, the fluorescence decreased with decreasing quantum dot concentration.

Example 8—Evaluation of GFAP Binding in Immunoassay

An assay, as described herein, comprising an "immunosandwich" of the target protein with the first and second molecule and quantum dot was prepared, as shown in FIG. 5, and analyzed using the microfluidic device described herein.

Reaction Protocol

Antibody Coupling to Magnetic Beads

The beads were resuspended in their stock solution by vortexing for 1-2 minutes. A 33 µL (1 mg) aliquot of beads were transferred to a tube. The tube was placed on a magnet for 4 minutes, and the supernatant was pipetted off. The beads were washed with 1 mL of C1 (supplied by ThermoFisher Scientific) and mixed by vortexing. The tube was placed on a magnet for 1 minute and the supernatant was removed. A 5 μg (5 μL) or 10 μpg (10 μL) aliquot of Abcam GFAP Capture Antibody was added to the beads. A 50 μL—antibody volume of C1 was added to the beads (5 μg aliquot → 45 μL and 10 μg aliquot→40 μL). A 50 μL aliquot of C2 was added to the tube and mixed by vortexing. The tube was incubated on a rocker at 37° C. overnight (16-24 hours).

The tube was placed on a magnet for 1 minute and the supernatant was removed. A 800 μL aliquot of HB+0.1% Tween 20 was added and mixed by shaking. The tube was placed on a magnet for 1 minute and the supernatant was removed. A 800 μL aliquot of LB+0.1%+Tween 20 was added and mixed by shaking. The tube was placed on a magnet for 1 minute and the supernatant was removed. A 800 μL aliquot of SB was added and mixed by shaking. The tube was placed on a magnet for 1 minute and the supernatant was removed. The beads were washed twice more, for a total of three washes. A 800 μL aliquot of SB was added and mixed by shaking. The tube was incubated with rotation at room temperature for 15 minutes. The tube was placed on a magnet and the supernatant was removed. The antibody-coupled beads were resuspended in 100 μL SB per mg of beads and stored at 2-8° C. (final concentration=10 mg/mL antibody-coupled beads).

Formation of the Multiplex

A 1 μL aliquot of the antibody-coated beads (epoxy beads coated with 5 μg of antibody) and 50 μL of PBS+0.1% Tween 20 were pipetted into a tube. The tube was placed on a magnet and the supernatant was removed. A 100 μL aliquot of sample (the desired concentration of GFAP in Blocking Buffer (1×PBS+0.1% BSA+0.05% Tween 20)) was added to the beads. The tube was incubated for 15 minutes at room temperature with rotation, and placed on a magnet to remove the supernatant. A 0.6 μL aliquot of Abcam Detector Antibody+2 μL of quantum dots+50 μL of PBS+0.1% Tween 20 were added to the beads, and incubated for 15 minutes at room temperature with rotation. The beads were washed 3 times with PBS+0.1% BSA and once with 1×PBS. The beads were resuspended in 100 μL of 1×PBS.

Trapping in Microfluidic Device

The channel of the microfluidic device was primed with 5% BSA in 1×PBS for 15 minutes (using a pressurized centrifuge tube to introduce the BSA solution into the channel). The centrifuge tube was emptied of any remaining BSA, and the processed beads (having the multiplex) were introduced to the centrifuge tube. The sample was loaded into the channel for 30 minutes. An image was captured using an inverted fluorescence microscope, CoolLED light source, and CCD camera. The fluorescence intensities of the trapped beads were analyzed using Fiji.

Figure 16:
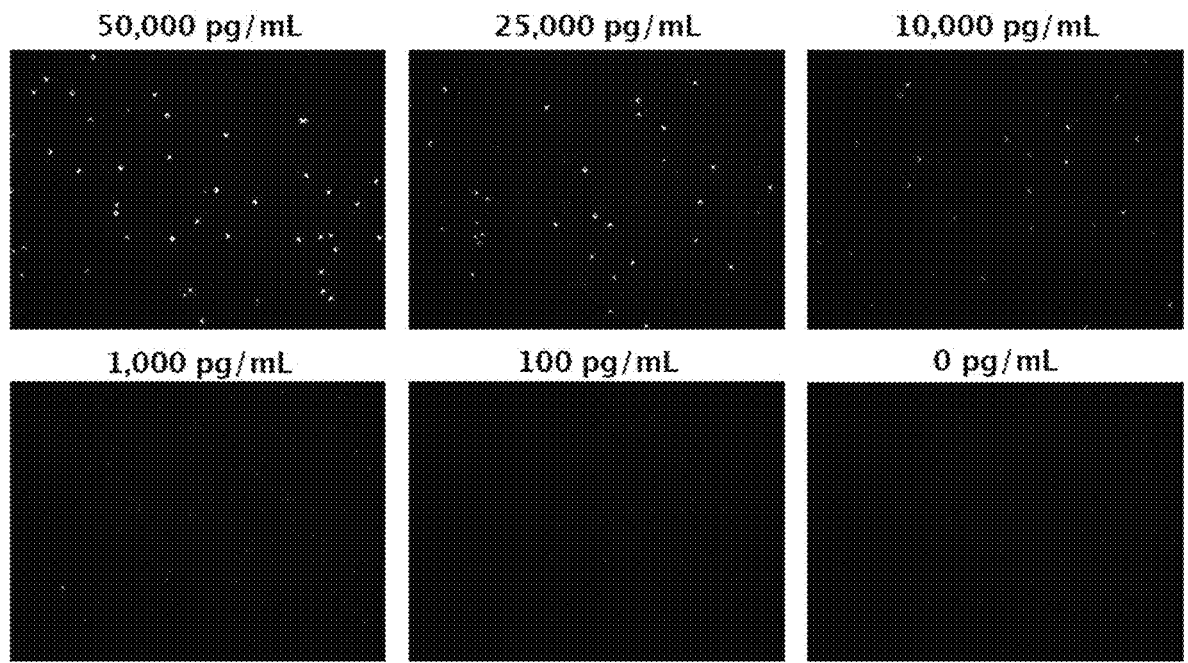
FIG. 16 shows fluorescence images of a GFAP protein associated with the surface of a bead as described herein.

The results from the fluorescent imaging are shown in FIG. 16, which demonstrate the immunoassay is effective in detecting GFAP in concentrations in the pg/mL and ng/mL scale. Therefore, Example 8 shows that the immunoassay of the disclosure has improved sensitivity over the commercial assay, and can be used with the microfluidic device to detect concentrations of GFAP that would be present in cerebrospinal fluid (CSF) (ng/mL) or in serum (pg/mL).

Example 9—Assay with Microfluidic Device

Figure 17:
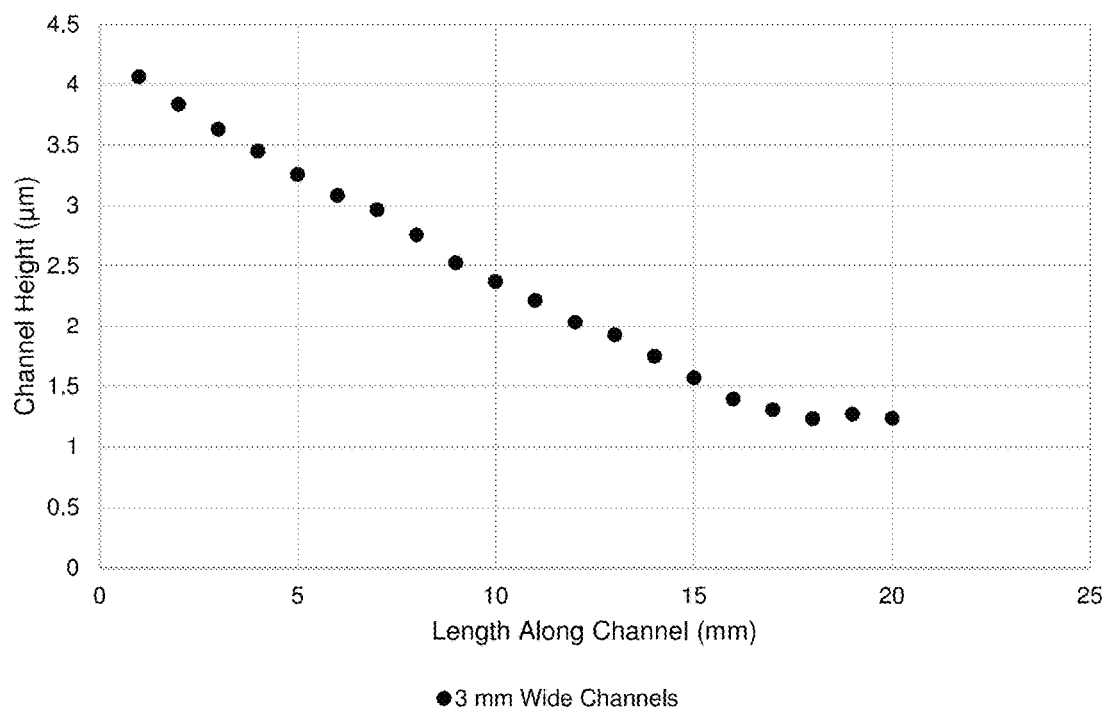
FIG. 17 is a graph of a height of a microfluidic device according to the disclosure.
Figure 18:
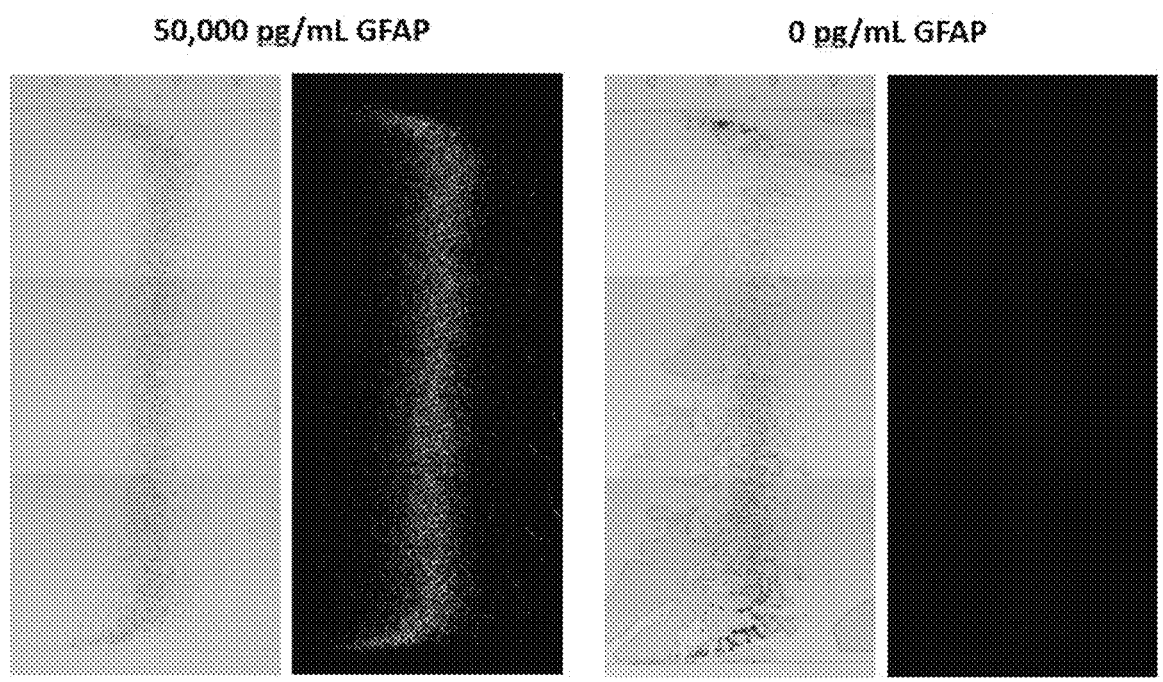
FIG. 18 shows fluorescence images of an assay described herein used in a microfluidic device disclosed herein.

A microfluidic device having height profile shown in FIG. 17 was used in connection with an assay as described herein:

Beads having multiplexes comprising GFAP (as the target protein) were trapped along the channel and fluorescence and brightfield images were obtained, as shown in FIG. 18.

Thus, Example 9 demonstrates that the microfluidic device and corresponding immunoassay can be used to detect GFAP in a sample at a concentration of about 50,000 pg/mL (50 ng/mL).

Example 10—Evaluation of IL-6 Binding in Immunoassay

An assay, as described herein, comprising an "immunosandwich" of the target protein with the first and second molecule and quantum dot was prepared, as shown in FIG. 6, and analyzed using the microfluidic device described herein.

Reaction Protocol

Antibody Coupling to Magnetic Beads

The beads were resuspended in their stock solution by vortexing for at least 30 seconds. A 200 μL aliquot of beads were transferred to a tube. The tube was placed on a magnet for 4 minutes, and the supernatant was discarded. The beads were washed with 1 mL of C1 (supplied by ThermoFisher Scientific) and mixed by vortexing. The tube was placed on a magnet for 1 minute and the supernatant was discarded. The tube was removed from the magnet and the washed beads were resuspended in 200 μL of C1.

The tube was placed on a magnet for 1 minute and the supernatant was discarded. The tube was removed from the magnet, and 40 μg (40 μL) of Abcam IL-6 Capture Antibody was added to the beads. A 100 μL—antibody volume of C1 was added to the beads (40 μg aliquot →60 μL). A 100 μL aliquot of C2 was added to the tube (total volume of 200 μL) and mixed by vortexing. The tube was incubated on a rocker at room temperature overnight (16-24 hours).

The tube was placed on a magnet for 1 minute and the supernatant was removed. A 800 μL aliquot of HB+0.1% Tween 20 was added and mixed by shaking. The tube was placed on a magnet for 1 minute and the supernatant was removed. A 800 μL aliquot of LB+0.1% Tween 20 was added and mixed by shaking. The tube was placed on a magnet for 1 minute and the supernatant was removed. A 800 μL aliquot of SB was added and mixed by shaking. The tube was placed on a magnet for 1 minute and the supernatant was removed. The beads were washed twice more, for a total of three washes. A 800 μL aliquot of SB was added and mixed by shaking. The tube was incubated with rotation at room temperature for 15 minutes. The tube was placed on a magnet and the supernatant was removed. The antibody-coupled beads were resuspended in 200 μL SB and stored at 2-8° C. (final mixture provided 8×10$^7$ beads in 200 μL).

Formation of the Multiplex

All reagents were allowed to come to room temperature. A 1 μL aliquot of the antibody-coated beads (M-450 epoxy beads coated with 40 μg of antibody) and 50 μL of PBS+1% Tween 20 were pipetted into a tube. The tube was placed on a magnet and the supernatant was removed. A 100 μL aliquot of sample (the desired concentration of IL-6 in Blocking Buffer (1×PBS+0.1% BSA+0.05% Tween 20)) was added to the beads. The tube was incubated for 15 minutes at room temperature with rotation, and placed on a magnet to remove the supernatant. A 1.44 μL aliquot of Abcam Detector Antibody+4 μL of quantum dots+50 μL of PBS+0.1% Tween 20 were added to the beads, and incubated for 15 minutes at room temperature with rotation. The beads were washed 3 times with PBS+0.1% BSA and once with 1×PBS. The beads were resuspended in 100 μL of 1×PBS.

What is claimed is:

1. A microfluidic device system (2) comprising:
a data collection and readout device (4) connected to a visual sensor (8), the visual sensor (8) operatively connected to a microfluidic device (10) for detection within the microfluidic device (10);
an inlet (132) by which a solution enters the microfluidic device (10), wherein the inlet (132) is connected to a supply line (14) that is connected to a container (12);
wherein the microfluidic device (10) further comprises a channel (126) having an entrance (128) and an exit (130), a height (H1) at the entrance (128) being greater than a height (H2) at the exit (130), and a height of the channel between the entrance and the exit has multiple decreases in height along a length of the channel between the entrance and the exit,
wherein:
the channel comprises at least a first length region having a continuously decreasing height, a second length region having a continuously decreasing height, and a step-wise decrease in height as a transition between the first length region and the second length region,
the height of the channel continuously decreases from a first height to a second height along an entire length of the first length region,
the height of the channel continuously decreases from a third height to a fourth height along an entire length of the second length region, and
the step-wise decrease comprises a decrease in the height of the channel from the second height to the third height, wherein the step-wise decrease in height occurs over a length of the channel that is less than one or both of the lengths of the first and second length regions.

2. The microfluidic device system (2) of claim 1, wherein the channel (126) has a width equal to or greater than 1000 µm.

3. The microfluidic device system of claim 1, wherein one or both of the first length region and the second length region has a decreasing height profile that is linear.

4. The microfluidic device of claim 1, wherein one or both of the first length region and the second length region has a quadratic decreasing height profile.

5. A method of using the microfluidic device system of claim 1, comprising:
introducing an anti-interaction agent to the channel of the microfluidic device (204);
introducing a solution to the channel of the microfluidic device, wherein the solution comprises cells or particles;
flowing the solution through the channel;
trapping the cells or particles within the channel;
stopping the flow of the solution through the channel;
capturing an image of the trapped cells or particles;
sending the image to a data collection/readout device;
analyzing the image using image software to determine size or deformability information about the trapped cells or particles.

6. The method of using the microfluidic device system of claim 5, wherein more than one image is captured, each image corresponding with a separate portion of the channel.

7. The method of using the microfluidic device system of claim 5, wherein the size or deformability information identifies a number of subsets having certain sizes or deformability characteristics.

8. The method of using the microfluidic device system of claim 7, wherein the size or deformability information further identifies the relative size of each of the number of subsets.

9. A method of fabricating the microfluidic device system of claim 1, comprising:
fabricating the microfluidic device, comprising:
preparing a glass wafer for etching;
etching the glass wafer by introducing the glass wafer into an etching solution at a specific rate with a first end of the glass wafer being etched longer than subsequent portions of the glass wafer;
performing additional etching on the glass wafer by submerging the entire glass wafer, including a previously un-etched portion of the glass wafer, in an etching solution; and
measuring the etched profile of the glass wafer to thereby fabricate the microfluidic device; and
operatively coupling the microfluidic device to the visual sensor.

10. The method of claim 9, further comprising:
drilling the inlet and an outlet to the microfluidic device (10) on a separate glass wafer;
bonding the separate glass wafer to the etched glass wafer (416).

11. The method of claim 9, wherein the etched profile has a target slope, and wherein the specific rate is determined based on the target slope.

12. A method for using the microfluidic device system of claim 1, comprising:
flowing an analysis solution through the channel, the analysis solution comprising a plurality of beads, each bead having a multiplex formed on a surface thereof, the multiplex being formed by association of first and second molecules with a target protein,
trapping each bead of the plurality of beads along the channel based on the diameter of the bead;
detecting the trapped plurality of beads with the visual sensor.

13. The method of claim 12, further comprising forming the analysis solution by combining a first solution with the target protein and a second solution, wherein
the first solution comprises the plurality of beads, each bead having a diameter and a surface substantially coated with the first molecule, and, the second solution comprises the second molecule associated with a quantum dot,
wherein the first molecule and the second molecule associate with the target protein to form the multiplex on the surface of each bead of the plurality of beads.

14. The method of claim 13, wherein the first solution, the target protein, and the second solution are combined prior to introduction into the microfluidic device.

15. The method of claim 14, wherein the first solution, the target protein, and the second solution are combined within the microfluidic device.

16. The method of claim 12, further comprising forming the analysis solution by introducing the target protein into the microfluidic device, the microfluidic device being pre-loaded with a solution comprising the plurality of beads, each bead having a diameter and a surface substantially coated with the first molecule, and the second molecule associated with a quantum dot.

17. The method of claim 12, wherein detecting the trapped plurality of beads comprises detecting a fluorescence of the multiplex on the surface of at least one of the trapped beads.

18. The method of claim 12, wherein detecting the trapped plurality of beads with the visual sensor comprises:
capturing an image of the trapped plurality of beads,
sending the image to the data collection/readout device; and
analyzing the image using image software to measure a fluorescence of the multiplex on the surface of at least one of the trapped beads located at one or more locations along the channel.

19. A microfluidic device system (2) comprising:
a data collection and readout device (4) connected to a visual sensor (8), the visual sensor (8) operatively connected to a microfluidic device (10) for detection within the microfluidic device (10);
an inlet (132) by which a solution enters the microfluidic device (10), wherein the inlet (132) is connected to a supply line (14) that is connected to a container (12);
wherein the microfluidic device (10) further comprises a channel (126) having an entrance (128) and an exit (130), a height (H1) at the entrance (128) being greater than a height (H2) at the exit (130), and a height of the channel between the entrance and the exit has multiple decreases in height along a length of the channel between the entrance and the exit,
wherein:
the channel comprises at least one region in which the height of the channel continuously decrease and at least one step-wise decrease in height, and
the height of the channel has continuously decreasing slope between the entrance and the exit.

* * * * *